US006417324B1

(12) United States Patent
Sällberg

(10) Patent No.: US 6,417,324 B1
(45) Date of Patent: Jul. 9, 2002

(54) SYNTHETIC PEPTIDES THAT BIND TO THE HEPATITIS B VIRUS CORE AND E ANTIGENS

(75) Inventor: Matti Sällberg, Älvsjo (SE)

(73) Assignee: Tripep AB, Huddinge (SE)

( * ) Notice: Subject to any disclaimer, the term of this patent is extended or adjusted under 35 U.S.C. 154(b) by 0 days.

(21) Appl. No.: 09/556,605

(22) Filed: Apr. 21, 2000

(51) Int. Cl.[7] .................. A61K 38/00; A61K 30/04; A61K 30/10; C07K 14/02; C12Q 1/20

(52) U.S. Cl. ............... 530/300; 500/350; 500/326; 435/5

(58) Field of Search .................. 530/300, 350, 530/326; 435/5

(56) References Cited

U.S. PATENT DOCUMENTS

| | | |
|---|---|---|
| 5,196,510 A | 3/1993 | Rodwell et al. |
| 5,869,232 A | 2/1999 | Sällberg |

FOREIGN PATENT DOCUMENTS

| | | |
|---|---|---|
| WO | WO 95/29938 | 11/1995 |
| WO | WO 98/03543 | 1/1998 |

OTHER PUBLICATIONS

Sequence alignment of Genseq sequence alignment of instant SEQ ID No. 28 with the antihuman parathyroid hormone-related protein of JP04228089-A. Kaneka Corp. Aug. 18, 1992. ID No. AR27008.*
Sequence alignment of Genseq sequence alignment of instant SEQ ID No: 29 with anti-DNA antibody 7b3 heavy chain variable region of WO 96/36361-A1. University of Michigan. Aug. 12, 1997. ID No. AAW04593.*
Sequence alignment of Genseq sequence alignment of instant SEQ ID No: 33 with anti-proenkephalin antibody PE-19 of WO 9606863-A1. University of Dundee. Oct. 9, 1996. ID No: AAR91370.*
GenCore sequnce alignment of SEQ ID No: 16 with the L-chain variable region of plasminogen activator antibody of JP61172900-A. Ashi Chemical Ind KK. Apr. 08, 1986. ID No: p. 61027.*
Lazdina, et al., *Journal of Virology*, 75(14):6367–6374, Jul. 2001.
Sällberg, et al., *Peptides: Chemistry and Biology*, pp. 715–718, 1993.
Skrivelis, et al., *Scand. J. Immunol.*, 37:637–643, 1993.
Steinbergs, et al., *Proceedings of the Latvian Academy of Sciences*, Section B, 50(2):74–77, 1996.
Database Genseq 'Online! Oct. 21, 1991, Asahi Chemical Ind. KK: "L-chain variable region of plasminogen activator antibody" XP002183673, Accession AAP61027 (published in JP11729000).
Database Genseq 'Online! Jan. 8, 1993, Clonatec SA: "Hepatitis B virus HBc antigen II", XP002183674, Accession AAR25272 (published in EP494825).
Database Genseq 'Online! Jul. 1, 1993, Cytel Corp: "Cytotoxic T-lymphocyte inducing peptide 802.03. " XP002183675, Accession AAR33488.

Database WPI, Section Ch, Week 199713, Derwent Publications Ltd., London, GB; Class B04, AN 1997–140911, XP002183678 & JP 09 020798 A (Asahi Kasei Kogyo KK), Jan. 21, 1997, abstract.
Database Patent_PRT 'Online! Mar. 21, 2001, Eurodiagnostica AB: "Sequence 9 from Patent W)0116163", XP002183677, Accession AX 090806.
Database Genseq 'Online! Jul. 31, 2000, Yeda Res & Dev Co Ltd: "Murine anti–Pab–421 IDI–1 mAb heavy chain CDR based Peptide IDI–H1", XP002183676, Accession AAY70799 (published in WO0023082).
Ganem, "Hepadnaviridae and Their Replication," *Fields Virology*, Third Ed., pp. 2703–2705, 1996.
Jin, et al;, "Expression, Isolation, and Characterization of the Hepatitis C Virus ATPase/RNA Hellcase," Archives of Biochemistry and Biophysics, 323:47–53, 1995.
Lee, et al., "Predominant Etiologic Association of Hepatitis C Virus with Hepatocellular Carcinoma Compared with Hepatitis B Virus in Elderly Patients in a Hepatitis B–Endemic Area," *Cancer*, 72:2564–2567.
Milich, et al., "The humoral immune response in acute and chronic hepatitis B virus infection." *Springer Semin. Immunopathol.* 17:149–166, 1995.
Milich, et al., "The Nucleocapsid of Hepatitis B Virus is Both a T–Cell–Independent and a T–Cell Dependent Antigen," *Science*, 234:1398–1401, 1986.
Milich, et al., "Role of B cells in antigen presentation of the hepatitis B core," *Proc. Natl. Acas. Sci USA*, 94:14648–14653, 1997.
Sällberg, et al., "Racid tea–bag' peptide synthesis using 9–fluorenylmethoxcarbonyl (Fmoc) protected amino acids applied for antigenic mapping of viral proteins," *Immunology Letters*, 30:59–68, 1991.
Sällberg, et al., "The Antigen/Antibody Specificity Exchanger: A New Peptide Based Tool for Re–directing Antibodies of Other Specificities to Recognize the V3 Domain of HIV–1 GP120," *Biochemical and Biophysical Research Communications*, 205:1386–1390, 1994.
Sällberg, et al., "Immunochemical structure of the carboxy–terminal part of hepatitis B e antigen: identification of internal and surface–exposed sequences," *Journal of General Virology*, 74: 1335–1340, 1993.
Schödel, et al., "Structure of Hepatitis B Virus Core and e–Antigen," *The Journal of Biological Chemistry*, 268:1332–1337, 1993.

* cited by examiner

*Primary Examiner*—James Housel
*Assistant Examiner*—Shanon A. Foley
(74) *Attorney, Agent, or Firm*—Knobbe, Martens, Olson & Bear, LLP

(57) ABSTRACT

The present invention relates generally to the field of virology. More particularly, the invention relates to the discovery that peptides, which bind to the Hepatitis B virus (HBV) core and e antigens, can be used to inhibit HBV infection. Embodiments concern "binding partners", which include peptides, peptidomimetics, and chemicals that resemble these molecules that interact with HBV core and e antigens, biological complexes having HBV core and e antigens joined to said binding partners, methods of identifying such binding partners, pharmaceuticals having binding partners, and methods of treatments and prevention of HBV infection.

15 Claims, No Drawings

SYNTHETIC PEPTIDES THAT BIND TO THE HEPATITIS B VIRUS CORE AND E ANTIGENS

FIELD OF THE INVENTION

The present invention relates generally to the field of virology. More particularly, the invention relates to the discovery that peptides that bind to the hepatitis B virus (HBV) core and e antigens can be used to inhibit HBV infection.

BACKGROUND OF THE INVENTION

Of the many viral causes of human hepatitis, few are of greater global importance than hepatitis B virus (HBV). Approximately 300 million people worldwide are chronically infected and some of these chronically infected individuals develop severe pathologic consequences including chronic hepatic insufficiency, cirrhosis, and hepatocellular carcinoma (HCC). (See *Fields Virology*, third ed., edited by Fields et al., Lipponcott-Raven Publishers, Philidelphia 1996 pp. 2703 and Lee et al., *Cancer*, 72:2564–7 (1993)). Primary infection may be asymptomatic (e.g,, in chronically infected individuals) or may result in varying degrees of acute liver injury. (Milich et al., *Springer Seminars in Immunopathology*, 17:149–66 (1995)).

HBV is unusual among animal viruses in that infected cells produce multiple types of virus-related particles. (See *Fields Virology*, third ed., edited by Fields et al., Lipponcott-Raven Publishers, Philidelphia 1996 pp. 2704). Electron microscopy of partially purified preparations of HBV shows three types of particles, a 42–47 nm infectious particle (referred to as "Dane particles"), non-infectious 20 nm spheres, and non-infectious 20 nm diameter filaments of variable length. Id. at 2705-2705. The HBV genome encodes at least five structural proteins: the envelope or surface proteins preS 1, preS2, and S (HBsAg); the polymerase; and the core or capsid antigen (HBcAg). All three forms of HBV particles have HBsAg, which serves as an epitope for neutralizing antibodies and is the basis for state of the art HBV diagnostics. In contrast, only the Dane particles have HBcAg, a 21 kD phosphoprotein that is believed to be phosphorylated in vivo. Id. at 2705. The HBV genome also encodes the non-structural proteins HBeAg and X. The HBcAg and the HBeAg are translated from two different mRNAs that are transcribed from the same open reading frame. The longer of the two mRNAs encodes HBeAg. HBcAg and the HBeAg share an amino acid sequence of approximately 150 residues.

HBcAg is highly immunogenic in humans and mice. Investigators have observed that HBcAg induces B-cells to produce IgM and, thus, is currently classified as a partially T cell independent antigen. (Milich and McLachlan, *Science*, 234:1398–401 (1986)). HBcAg can also crosslink B-cell surface receptors and membrane bound IgM on naive B-cells and, in turn, HBcAg can be taken up, processed, and presented to HBcAg-specific CD4⁻T cells. (Milich et al., *Proc Natl Acad Sci USA*, 94:14648–14653 (1997)). Quite surprisingly, B-cells that are able to bind and present HBcAg exist in great numbers in naive non-immunized mice. The identification of molecules that inhibit HBV infection by interacting with HBcAg and/or HBeAg remains a largely unrealized goal.

BRIEF SUMMARY OF THE INVENTION

The invention described herein concerns the identification and manufacture of molecules that interact with HBcAg and/or HBeAg and thereby inhibit HBV infection or modulate a host immune system response or both. Molecules that interact with HBcAg and/or HBeAg, also referred to as "binding partners", are designed from fragments of antibodies and other proteins that interact with HBcAg and/or HBeAg. Accordingly, an amino acid sequence corresponding to the binding domains of monoclonal or polyclonal antibodies or proteins that bind HBcAg and/or HBeAg is used as a template for the design of synthetic molecules, including but not limited to, peptides, derivative or modified peptides, peptidomimetics, and chemicals. A preferred binding partner, for example, is a molecule called a "specificity exchanger", which comprises a first domain that interacts with HBcAg and/or HBeAg and a second domain that has an epitope for a high titer antibody, preferably an epitope on a pathogen or a toxin. The binding partners described herein can be manufactured by conventional techniques in peptide chemistry and/or organic chemistry.

Methods to characterize binding partners are also embodiments. The term "characterization assay" is used to refer to an experiment or evaluation of the ability of a candidate binding partner and/or binding partner to interact with HBcAg and/or HBeAg, inhibit HBV infection, or modulate a host immune response. Some characterization assays, for example, evaluate the ability of a binding partner to bind to a multimeric agent having HBcAg and/or HBeAg disposed thereon or vice versa. Other characterization assays access the ability of a binding partner to fix complement and/or bind to a high titer antibody. Additional characterization assays determine whether a binding partner can effect viral infection in cultured cell lines or infected animals. Still further, some embodiments evaluate the ability of a binding partner to modulate a host immune system response, as measured by cytokine production and/or T cell proliferation.

Binding partners can be used as immunochemicals for the detection of HBcAg and/or HBeAg and can be incorporated into diagnostic methods and kits. Binding partners, preferably specificity exchangers, can also be incorporated into pharmaceuticals and used to treat or prevent HBV infection. A preferred embodiment concerns a method of treating or preventing HBV infection by identifying a subject in need and administering said subject a therapeutically effective amount of binding partner.

As described herein, embodiments include a peptide that binds HBcAg or HBeAg having about 3–50 amino acids residues. Preferably, the sequence of said peptide is selected from the group consisting of SEQ. ID. Nos. 4–45, 53, 54, 66–69, 71, and 74. Other embodiments include a peptide comprising the sequence of at least one of SEQ. ID. Nos. 1–3, a peptide comprising the sequence of SEQ. ID. No. 45, a peptide comprising the sequence of SEQ. ID. No. 54, a peptide comprising the sequence of SEQ. ID. No. 74, and a peptide having a specificity domain, which binds HBcAg or HBeAg and an antigenic domain joined to the specificity domain, wherein said antigenic domain binds a high titer antibody, preferably an epitope for a pathogen or toxin.

Related embodiments concern a peptidomimetic that corresponds to a peptide selected from the group consisting of SEQ. ID. No. 1, 2, 3, 45, 54, and 74 and an isolated or purified peptide that is less than 50 amino acids in length having the formula: $X^1{}_n CKASX^2{}_n$, wherein "$X^1$" and "$X^2$" are any amino acid and "n" is any integer, and wherein the molecule specifically binds HBcAg and/or HBeAg. Another way of describing the molecules of this class is by the formula: "$X^1{}_n CZASX^2{}_n$", wherein: "$X^1$" and "$X^2$" are any amino acid and "n" is any integer, "C" is cysteine, "Z" is lysine or arginine", "A" is alanine, and "S" is serine. In some embodiments, the "$X^1_n$" or "$X^2_n$" encodes an epitope that binds a high titer antibody (e.g., an epitope on a pathogen or a toxin). Other embodiments include an isolated or purified peptide that is less than 50 amino acids in length having the formula: $X^1_n CRASX^2_n$, wherein "$X^1$" and "$X^2$" are any amino acid and "n" is any integer, and wherein the molecule specifically binds HBcAg and/or HBeAg. As above, another way of describing the molecules of this class is by the formula: "$X^1_n CZASX^2_n$", wherein: "$X^1$" and "$X^2$" are any amino acid and "n" is any integer, "C" is cysteine, "Z" is lysine or arginine", "A" is alanine, and "S" is serine. In some embodiments, "$X^1_n$" or "$X^2_n$" encodes an epitope that binds a high titer antibody. Additional embodiments include a nucleic acid encoding a peptide selected from the group consisting of SEQ. ID. Nos. 1, 2, 3, 45, 54, and 74.

Some embodiments include a method of making a binding partner that interacts with HBcAg or HBeAg. By one approach, a region of a polypeptide that interacts with HBcAg or HBeAg is identified, the sequence of said region of the polypeptide is determined, and a synthetic or recombinant binding partner that corresponds to the sequence of said region of the polypeptide is produced. In some aspects of this embodiment, the polypeptide is an antibody and, in other aspects, the binding partner is a specificity exchanger. More embodiments include methods of making a pharmaceutical. By one approach, a binding partner that interacts with HBcAg or HBeAg is identified and a therapeutically effective amount of said binding partner is incorporated into a pharmaceutical. In preferred aspects of this method, the binding partner has a sequence selected from the group consisting of SEQ. ID. Nos. 4–45, 53, 54, 66–69, 71, and 74. Another method described herein concerns an approach to treat or prevent HBV infection. Accordingly, a subject in need of a molecule that inhibits HBV infection is identified and said subject is provided a binding partner that interacts with HBcAg or HBeAg, or both. Preferred aspects of this method involve a binding partner that has a sequence selected from the group consisting of SEQ. ID. Nos. 4–45, 53, 54, 66–69, 71, and 74.

Methods of identifying a binding partner that interacts with HBcAg or HBeAg are also embodiments. By one approach, a support comprising HBcAg or HBeAg is provided, the support is contacted with a candidate binding partner, and a biological complex comprising HBcAg or HBeAg and the candidate binding partner is detected, wherein detection of such complex indicates that said candidate binding partner is a binding partner interacts with HBcAg or HBeAg. In preferred aspects of this embodiment, the candidate binding partner has an amino acid sequence selected from the group consisting of SEQ. ID. Nos. 1–78. Another method of identifying a binding partner that inhibits HBV infection involves providing a cell that is infected with HBV, contacting said cell with a candidate binding partner, and identifying said binding partner when the presence of said candidate binding partner with said cell is associated with a decrease in HBV infection.

Furthermore, methods are provided that identify a binding partner that modulates an immune system response. Accordingly, one method is practiced by providing a naive antigen presenting cell, contacting said naive antigen presenting cell with a binding partner and a T cell that reacts to HBcAg or HBeAg, and detecting an inhibition or enhancement of T cell stimulation. In some embodiments, the detection step is performed by evaluating a change in cytokine production or T cell proliferation.

In another embodiment, a computerized system for identifying a binding partner that interacts with HBcAg or HBeAg is provided. This system includes a first data base comprising protein models of HBcAg or HBeAg; a second data base comprising the composition of a plurality of candidate binding partners; a search program that compares the protein model of the first data base with the compositions of the candidate binding partners of the second database; and a retrieval program that identifies a binding partner that interacts with the protein model of the first database. In some aspects of this embodiment, the candidate binding partners have an amino acid sequence selected from the group consisting of SEQ. ID. Nos. 1–78.

Additionally, a computer-based system for identifying a candidate binding partner having homology to a binding partner is provided. This system has a database with at least one of the sequences of SEQ ID NOS: 1–78 or a representative fragment thereof, a search program that compares a sequence of a candidate binding partner to sequences in the database to identify homologous sequence(s), and a retrieval program that obtains said homologous sequence(s).

A method of determining the presence of HBV in a biological sample is also an embodiment. This method is practiced by providing a biological sample, providing a binding partner that binds to HBcAg and/or HBeAg, wherein said binding partner has a sequence selected from the group consisting of SEQ. ID. Nos. 4–45, 53, 54, 66–69, 71, and 74, and determining the presence of HBV in the biological sample by monitoring whether said binding partner binds to HBcAg and/or HBeAg. Diagnostic kits for the detection of HBV infection are embodiments, as well. One such kit has a binding partner, wherein said binding partner has a sequence selected from the group consisting of SEQ. ID. Nos. 4–45, 53, 54, 66–69, 71, and 74.

DETAILED DESCRIPTION OF THE INVENTION

The disclosure herein describes the manufacture, characterization, and use of molecules that bind hepatitis B virus (HBV) core (HBcAg) and e (HBeAg) antigens and thereby inhibit HBV infection and/or modulate a host immune system response. The molecules that bind to HBcAg and/or HBeAg, such as peptides, modified or derivatized peptides, peptidomimetics, and chemicals, are collectively referred to as "binding partners". Binding partners can be obtained by synthesizing the heavy (VH) and light (VL) chains of antibodies (e.g., polyclonal, monoclonal, or fragments thereof), synthesizing the domains of proteins that interact with HBcAg and/or HBeAg, and by employing techniques in rational drug design and combinatorial chemistry.

Several synthetic peptides, derived from the variable domains of monoclonal antibodies (mAbs) specific for the hepatitis B virus HBcAg and/or HBeAg, were obtained as follows. The mnRNAs encoding the VH and VL chains of HBcAg and/or HBeAg monoclonal antibodies (mAbs) were sequenced and the protein sequences corresponding to these mRNAs were determined. Several synthetic peptides corresponding to these sequences were then synthesized using conventional protein chemistry. These "candidate binding partners", which have the potential to bind HBcAg and/or HBeAg, were tested for the ability to interact with HBcAg and HBeAg. Five peptides, in particular, were discovered to bind HBcAg and/or HBeAg with high affinity and these "high affinity" binding partners had either the conserved motif "CKAS" (SEQ. ID. No. 77) or "CRAS" (SEQ. ID. No. 78). Thus, preferred embodiments include peptides, derivative or modified peptides, or peptidomimetics having the formula "$X^1_n CKASX^2_n$" or "$X^1_n CRASX^2_n$", wherein "$X^2$" and "$X^2$" are any amino acid and "n" is an integer, that bind HBcAg and/or HBeAg. Another way of describing the molecules of this class is by the formula: "$X^1_n CZASX^2_n$", wherein: "$X^1$" and "$X^2$" are any amino acid and "n" is any integer, "C" is cysteine, "Z" is lysine or arginine", "A" is alanine, and "S" is serine.

By a similar approach, synthetic peptides corresponding to the binding domains of polyclonal antibodies specific for HIBcAg and/or HBeAg can be manufactured. Polyclonal antibodies specific for HBcAg and/or HBeAg are generated by inoculating animals with HBcAg and/or HBeAg. The mRNAs encoding the polyclonal antibodies are isolated, sequenced, and the protein sequences corresponding to these mRNAs are determined. Synthetic peptides corresponding to these protein sequences are then made using conventional techniques in protein chemistry. Several strategies for obtaining the imRNAs that encode polyclonal antibodies that bind HBcAg and/or HBeAg are contemplated including, but not limited to, yeast one-hybrid screens, yeast two-hybrid screens, and phage display techniques. Ideally, cDNA expression libraries corresponding to mRNAs encoding polyclonal antibodies that bind HBcAg and/or HBeAg are created. Embodiments that employ such libraries can express recombinant binding partners, which can be isolated or purified, characterized, and used in lieu of or in addition to synthetic binding partners.

The term "isolated" requires that the material be removed from its original environment (e.g., the natural environment if it is naturally occurring). For example, a naturally-occurring polypeptide present in a living animal is not isolated, but the same polypeptide, separated from some or all of the coexisting materials in the natural system, is isolated. It is also advantageous that the sequences be in purified form. The term "purified" does not require absolute purity; rather, it is intended as a relative definition. Isolated proteins have been conventionally purified to electrophoretic homogeneity by Coomassie staining, for example. Purification of starting material or natural material to at least one order of magnitude, preferably two or three orders, and more preferably four or five orders of magnitude is expressly contemplated.

In addition to antibodies and peptides derived from antibodies, other molecules that bind HBcAg and/or HBeAg can be identified by the methods described herein. That is, techniques in high throughput screening, combinatorial chemistry, and rational drug design can be employed to identify more binding partners. By one approach, for example, a high throughput screen based on a yeast two hybrid system is employed.

Accordingly, cDNA expression libraries are generated from any organism (e.g., plant, bacteria, virus, insect, amphibian, reptile, bird, or mammal) or a plurality of such organisms or from random or directed oligonucleotide synthesis. In some embodiments, the organism will have been immunized for HBcAg and/or HBeAg prior to creation of the cDNA expression library. To create the cDNA library for the yeast two-hybrid screen, isolated cDNA made from total mRNA obtained from the organism or generated by oligonucleotide synthesis is cloned into a first expression construct having a nucleic acid encoding a transcriptional activation domain (e.g., GAL4). As one of skill will appreciate, the cloning of the first expression construct is conducted such that cells having the construct will express a fusion protein comprising the cDNA of interest and the transcriptional activation domain when induced.

Next, a second expression construct (referred to as the "bait") is made. This construct has nucleic acid encoding HBcAg and/or HBeAg or fragments thereof joined to a transcriptional binding domain (e.g., GAL4). When a cell having the second expression construct is properly induced, a second fusion protein comprising the HBcAg and/or HBeAg or fragments thereofjoined to the transcriptional binding domain (the "bait") is expressed. The two expression constructs are transferred into yeast, which harbor a DNA template having at least one DNA binding domain specific for the transcriptional binding domain encoded by the bait construct, a minimal promoter, and a downstream reporter gene (e.g., Lac Z or Green Fluorescent Protein (GFP)). When a peptide from the cDNA library (i.e., the fusion protein expressed from the first construct) binds to the bait (i.e., the fusion protein from the second construct) a detectable signal is generated from the reporter gene. The yeast clones can be presented in addressable arrays, which allows for the precise determination of the clone containing an insert that encodes a protein that binds HBcAg and/or HBeAg. In this manner, protein/protein interactions between HBcAg and/or HBeAg and the proteins expressed from the cDNA library can be rapidly identified.

Clones that display a signal after induction of the first and second constructs but fail to produce a signal without induction are isolated, amplified, and the cDNA inserts are sequenced. The nucleic acid sequence information can be converted to an amino acid sequence and peptides corresponding to these sequences can be synthesized by conventional protein chemistry. Alternatively, recombinant peptides expressed from the positive clones can be isolated and/or purified. These candidate binding partners can then be screened for the ability to interact with HBcAg and/or HBeAg. The binding partners identified by the approaches above can also be used as templates for the design of modified or derivative peptides, peptidomimetics, and for rational drug design. For example, computer modeling and combinatorial chemistry can be employed to design and manufacture derivative binding partners.

The term "binding partner" also refers to a bi-functional binding partner or "specificity exchanger" comprising a "specificity domain", which binds HBcAg and/or HBeAg, and an "antigenic domain", which binds an antibody or other molecule that can be unrelated to a molecule that binds HBcAg and/or HBeAg. These bi-functional binding partners can redirect antibodies that already exist in an organism to a desired antigen. Such specificty exchangers can be manufactured by joining a molecule that binds HBcAg and/or HBeAg, such as a binding partner identified by a method described above, to an epitope for any antibody using conventional techniques in molecular biology. In one embodiment, for example, a specificity domain comprising the CKAS (SEQ. ID. No. 77) motif was joined to an antigenic domain comprising the epitope for a monoclonal antibody specific for the herpes simplex virus type 1 gG2 (HSVgG2) protein.

Desirably, the binding partners are evaluated in a "characterization assay", which determines the ability of the molecule to interact with HBcAg and/or HBeAg, inhibit HBV infectivity, or modulate (inhibit or enhance) a host immune system response. Several characterization assays described herein involve binding assays that analyze whether a binding partner can interact with HBcAg and/or HBeAg and to what extent a binding partner can compete with other ligands for HBcAg and/or HBeAg (e.g., multimeric support-based assays and computer generated binding assays). Additionally, some characterization assays determine the efficacy of binding partners as inhibitors of HBV infection in vitro and in vivo. Further, characterization assays are designed to analyze whether a binding partner can modulate a host immune system response, as indicated by the activation of an antigen presenting cell (e.g., a B cell or dendritic cell), production of a cytokine, or T cell proliferation.

The binding partners can be used as biotechnological tools, diagnostic reagents, and the active ingredients in pharmaceuticals. In some embodiments, for example, the binding partners are used as detection reagents in conventional immunohistochemical techniques. In other embodiments, the binding partners are expressed in a cell in vitro or in vivo. Still in other embodiments, the binding partners are used as diagnostic reagents to detect the presence or absence of HBV in a biological sample obtained from a subject. According to this later aspect, the binding partners can also be used to determine the efficacy of an HBV treatment protocol by monitoring the levels of HBcAg and/or HBeAg before, during, and after treatment.

Further, binding partners can be incorporated into pharmaceuticals that can be administered to subjects in need of an agent that interacts with HBcAg and/or HBeAg, such as a human in need of treatment and/or prevention of HBV infection. Preferably, these pharmaceuticals comprise formulations having a specificity exchanger that promotes rapid clearance of HBV particles. Additionally, the pharmaceuticals can include nucleic acid constructs manufactured such that binding partners (preferably specificity exchangers) are expressed in a variety of cells of the body. The pharmaceuticals can be administered to individuals in need of treatment and/or prevention of HBV infection. The section below describes several approaches to identify and manufacture binding partners specific for HBcAg and/or HBeAg.

Identification and manufacture of binding partners specific for HBcAg and/or HBeAg In general, the approach to make the binding partners described herein involves: (1) obtaining molecules that bind to HBcAg and/or HBeAg; (2) determining the molecular structure or sequence of said molecules; and (3) synthesizing peptides that have said molecular structure or sequence. In one aspect, for example, antibodies or other peptides that bind to HBcAg and/or HBeAg are generated and/or identified; the mRNA sequence encoding the binding partner is obtained, converted to cDNA, and sequenced; and, from this sequence, peptides are synthesized. The HBcAg and HBeAg-specific peptides can be modified, derivatized, and can also be used as templates for the design of peptidomimetics and rational drug discovery. Through techniques in combinatorial chemistry and rational drug design, many more binding partners can be identified. The term "binding partner" refers to a molecule that binds HBcAg and/or HBeAg, and should be distinguished from the term "candidate binding partner", which refers to a molecule that potentially binds to HBcAg and/or HBeAg. Desirably, binding partners inhibit viral infectivity and/or modulate (inhibit or enhance) a host immune system response (e.g., antigen presenting cell activation, cytokine production, and/or T cell proliferation).

By one approach, the design and manufacture of peptides that bind HBcAg and HBeAg involves the manufacture of mAbs directed to HBcAg and HBeAg. Depending on the context, the term "antibodies" can encompass polyclonal, monoclonal, chimeric, single chain, Fab fragments and fragments produced by a Fab expression library. Furthermore, the terms "low titer antibody" and "high titer antibody" are also used to refer to an antibody having a low avidity to an antigen and a high avidity to an antigen, respectively. That is, whether a particular antibody is a "low titer antibody" or a "high titer antibody" depends on the dilution of antibody containing sera at which an antigen is no longer detectable in an enzyme immunoassay (e.g., an enzyme immunoassay (EIA) or ELISA assay); 200 ng of target antigen is typically used with a 1:1000 dilution of secondary antibody. Thus, a "low titer antibody" generally no longer detects an antigen at a dilution that is less than 1:10000 under the conditions for ELISA described above and a "high titer antibody" is characterized by the ability to detect an antigen at a dilution that is greater than or equal to 1:10000.

For the production of antibodies, whether monoclonal or polyclonal, various hosts including goats, rabbits, rats, mice, etc. can be immunized by injection with HBcAg and/or HBeAg or any portion, fragment or oligopeptide that retains immunogenic properties. Depending on the host species, various adjuvants can be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and Corynebacterium parvum are also potentially useful adjuvants.

Peptides used to induce specific antibodies can have an amino acid sequence consisting of at least three amino acids, and preferably at least 10 to 15 amino acids. Short stretches of amino acids encoding fragments of HBcAg and/or HBeAg can be fused with those of another protein such as keyhole limpet hemocyanin such that an antibody is produced against the chimeric molecule. While antibodies capable of specifically recognizing HBcAg and/or BBeAg can be generated by injecting synthetic 3-mer, 10-mer, and 15-mer peptides that correspond to a protein sequence of a binding partner into an appropriate organism, a more diverse set of antibodies are generated by using recombinant HBcAg and/or HBeAg.

Monoclonal antibodies directed to HBcAg and/or HBeAg can be prepared using any technique that provides for the production of antibody molecules by continuous cell lines in culture. These include, but are not limited to, the hybridoma technique originally described by Koehler and Milstein (*Nature* 256:495–497 (1975)), the human B-cell hybridoma technique (Kosbor et al. *Immunol Today* 4:72 (1983); Cote et al *Proc Natl Acad Sci* 80:2026–2030 (1983), and the EBV-hybridoma technique Cole et al. *Monoclonal Antibodies and Cancer Therapy*, Alan R. Liss Inc, New York N.Y., pp 77–96 (1985)). In addition, techniques developed for the production of "chimeric antibodies", the splicing of mouse antibody genes to human antibody genes to obtain a molecule with appropriate antigen specificity and biological activity can be used. (Morrison et al. *Proc Natl Acad Sci* 81:6851–6855 (1984); Neuberger et al. Nature 312:604–608 (1984); Takeda et al. *Nature* 314:452–454(1985)). Alternatively, techniques described for the production of single chain antibodies (U.S. Pat. No. 4,946,778) can be adapted to produce HBcAg and/or HBeAg-specific single chain antibodies. Antibodies can also be produced by inducing in vivo production in the lymphocyte population or by screening recombinant immunoglobulin libraries or panels of highly specific binding reagents as disclosed in Orlandi et al., *Proc Natl Acad Sci* 86: 3833–3837 (1989), and Winter G. and Milstein C; *Nature* 349:293–299 (1991).

Antibody fragments that contain specific binding sites for HBcAg and/or HBeAg can also be generated. For example, such fragments include, but are not limited to, the $F(ab')_2$ fragments that can be produced by pepsin digestion of the antibody molecule and the Fab fragments that can be generated by reducing the disulfide bridges of the F(ab')$_2$ fragments. Alternatively, Fab expression libraries can be constructed to allow rapid and easy identification of monoclonal Fab fragments with the desired specificity. (Huse W. D. et al. *Science* 256:1275–1281 (1989)).

By one approach, monoclonal antibodies to HBcAg and/or HBeAg or fragments thereof are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution are placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, N.Y. Section 21–2. By using the approach described in Example 1, several monoclonal antibodies specific for HBcAg and/or HBeAg were made.

EXAMPLE 1

The mAbs that were used to create the binding partners specific for HBcAg and/or HBeAg were made by conventional techniques, as described above, using recombinant peptides. Full length recombinant HBcAg (rHBcAg) encompassing residues 1–183 was produced in *Escherichia coli* as previously described. (Schodel et al., *J Biol Chem*, 268:1332–7 (1993), herein expressly incorporated by reference in its entirety). A truncated recombinant form of HBeAg containing nine residues of pre-core and the 150 first residues of HBcAg was also made. Further, a non-structural 3 protein (NS3) of the hepatitis C virus (HCV) was also made to serve as a control. (Jin and Peterson, *Arch. Biochem. Biophys.*, 323:47–53 (1995), herein expressly incorporated by reference in its entirety). Another control peptide, an analogue of HBcAg (ΔHBcAg), wherein region 76–85 was replaced by an irrelevant sequence, was also made.

Balb/c and CBA mice (purchased from BK Universal, Sollentuna, Sweden) were immunized (Freunds complete adjuvant; CFA) and boosted (Freunds incomplete adjuvant; IFA) by 10 μg of the recombinant peptides. The mice were immunized one to three times, with two weeks between each immunization. Three days after the last injection, spleen cells were harvested and fused with the SP2/0 myeloma cells by standard procedures. The SP2/0 cell lines expressing mAbs were maintained in RPMI-1640 medium supplemented with 10% FCS, 2 mM L-Glutamine, 100 U/ml Penicilin and 100 μg/ml Streptomycin (GIBCO-BRL, Gaithesburgh, Md.). All cells were incubated at 37° C. with 7% CO$_2$. Following three cycles of cloning and screening by enzyme immunoassay (EIA) using the indicated antigens, stable hybridomas were selected for antibody analysis and extraction of mRNA. The antibodies were purified on immobilized protein A/G (Pierce, Rockford, Ill.). By using the approach described in this example, several mAbs that bind HBcAg and/or HBeAg were obtained.

Four of the mAbs obtained by the approach described in Example 1 were characterized for their reactivity to HBcAg, ΔHBcAg, denaturated HBcAg, and HBeAg. The example below describes the approach that was used to characterize the reactivity of mAbs directed to HBcAg and/or HBeAg.

EXAMPLE 2

To determine the reactivity and specificity of a mAb, recombinant proteins or fragments thereof (e.g., HBcAg, HBeAg, ΔHBcAg, denatured HBcAg, or NS3 proteins) were passively adsorbed at 10 μg/ml to 96 well microtiter plates in 50 mM sodium carbonate buffer, pH 9.6, overnight at 4° C. Serial dilutions of mAbs were made in phosphate buffered saline (PBS) containing 2% goat serum (Sigma Chemicals, St Louis, Mo.), and 0.05% Tween 20 (PBS-GT). The various dilutions were then incubated on the plates for 60 minutes. Bound mabs were detected either by rabbit anti-mouse IgG (Sigma), or rabbit anti-mouse IgG1, IgG2a, IgG2b or IgG3 (Sigma) followed by a peroxidase labeled goat anti-rabbit IgG (Sigma). The plates were developed by incubation with dinitro-phenylene-diamine (Sigma) and the absorbance at 405 nm was determined. The results of these studies are provided in Table 1.

TABLE 1

MAb reactivity to HBcAg, mutant HBcAg (ΔHBcAg), denaturated HBcAg (dHBcAg), and HBeAg*.

| MAb | Endpoint titre to indicated antigen | | | | Dominating specificity |
| --- | --- | --- | --- | --- | --- |
| | HBcAg | ΔHBcAg | dHBcAg | HBeAg | |
| 3-4 | 3,125 | 1 | 1 | 15,625 | HBeAg |
| 4-2 | 3,125 | 625 | 15,625 | 125 | dHBcAg |
| 5H7 | 625 | 0 | 1 | 1 | HBcAg |
| 9C8 | 78,125 | 25 | 25 | 25 | HBcAg |

*Values are given as the endpoint titres (the highest dilution giving an OD at 490 nm of three times the negative control).

Once the specificity of binding of the mAbs was determined, the mRNAs encoding the VH and/or VL domains of three mAbs (i.e., mAbs 4-2, 5H7, and 9C8) were sequenced and these mRNA sequences were converted to protein sequences. The next example describes the method that was used to determine the protein sequence of a binding domain of an antibody that interacts with HBcAg and/or HBeAg.

EXAMPLE 3

To determine the protein sequence of an antibody binding domain, total cellular mRNA was extracted using magnetic beads coated with oligo-dT25 (Dynal A. S, Oslo, Norway). The variable domains of the heavy (VH) and light (VL) chains of mAbs were amplified from cDNA by the Polymerase Chain Reaction (PCR) using the recombinant phage antibody system (Pharmacia Biotech, Uppsala, Sweden). The amplified CDNA fragments were directly ligated to the TA cloning vector pCR 2.1 (Invitrogen, San Diego, USA) as described. (Zhang et al., *Clin. Diagn. Lab. Immunol.*, 7:58–63 (2000), herein expressly incorporated by reference in its entirety). The DNA sequences were determined by an automated sequencer (ALF express, Pharmacia, Uppsala, Sweden) as described. (Zhang et al., *Clin. Diagn. Lab. Immunol.*, 7:58–63 (2000), herein expressly incorporated by reference in its entirety). From the cDNA sequence, a corresponding protein sequence was deduced. The protein sequences deduced from VH cDNA clones of mAbs 4-2 and 9C8 and VL cDNA clone 5H7 are provided in Table 2 and in the Sequence Listing (SEQ. ID. Nos. 1–3). The approach described above can be used to determine the protein sequence of the binding domain of either a monoclonal or polyclonal antibody.

TABLE 2

The deduced VH and/or VL sequences of mAbs 4-2, 5H7 and 9C8.

4-2 VH
VKLQQSGTEVVKPGASVKLSCKASGYIFTSYDIDWVRQTPEQGLEWIGWIFPGE (SEQ.ID.No.1)
GSTEYNEKFKGRATLSVDKSSSTAYMELTRLTSEDSAVYFCARGDYDYYRRYF
DLWGQGTTVTVS

5H7 VL
DIVLTQSPASLAVSLGQRATISCRASQSVSTSSYSYMHWYQQKPGQPPKLLIKY (SEQ.ID.No.2)
ASNLESGVPARFSGSGSGTDFTLNIHPVEEEDTATYYCQHSWEIPYTFGGGTKLE
IKRADAAPAVSIFPPSSKLG

9C8 VH
IQLQQSGAELVKPGASVKISCKASGYSFTGYNMNWVKQSHGKSLEWIGNJNPY (SEQ.ID.No.3)
YGSTSYNQKFKGKATLTVDKSSSTAYMQLNSLTSEDSAVYYCARGKGTGFAY
WGQGTLVTVSAAKTTPPSVYPLVPV

Synthetic peptides corresponding to the VH and/or VL sequences of mAbs 4-2, 5H7, and 9C8 or fragments thereof were then synthesized by conventional techniques in protein chemistry. These synthetic peptides are referred to as "candidate binding partners" because they are molecules that potentially bind HBcAg and/or HBeAg. The example below describes an approach that was used to synthesize a peptide that corresponds to the binding domain of a mAb specific for HBcAg and/or HBeAg.

EXAMPLE 4

Peptides that correspond to regions of a binding domain of a mab specific for HBcAg and/or HBeAg were manufactured as follows. Overlapping peptides (20 amino acids long with a 10 amino acid residue overlap) corresponding to the VH and/or VL of the mAbs 4-2, 5H7, and 9C8 were produced by standard techniques (Sällberg et al., *Immunol Lett,* 30:59–68 (1991), herein expressly incorporated by reference in its entirety) using a multiple peptide synthesizer and standard Fmoc chemistry (Syro, MultiSynTech, Germany). Additional deletion and alanine substitution analogues of reactive peptides were synthesized by the same technique. In some cases the peptides were purified by high performance liquid chromatography using standard protocols. (Sällberg et al., *Immunol Lett,* 30:59–68 (1991), herein expressly incorporated by reference in its entirety). There are many ways to synthesize or produce the peptides described herein (e.g., through recombinant technology) and the approach described above is one such method.

In addition to using monoclonal antibodies, the design and manufacture of peptides that bind HBcAg and HBeAg can involve the manufacture of polyclonal antibodies directed to HBcAg and HBeAg. Accordingly, animals are repetitively inoculated with HBcAg and/or HBeAg so as to raise a population of high titer polyclonal antibodies specific for HBcAg and/or HBeAg. The mRNAs that encode the polyclonal antibodies are isolated, converted to cDNA, and the protein sequences corresponding to these cDNAs are deduced. (See Examples 3 and 4, for an approach to manufacture peptides that correspond to a binding domain of an antibody). Synthetic peptides having these protein sequences are then made using conventional techniques in peptide chemistry.

Polyclonal antiserum containing antibodies to heterogenous epitopes of a single protein can be prepared by immunizing suitable animals with HBcAg and/or HBeAg or fragments thereof, which can be unmodified or modified to enhance immunogenicity. Effective polyclonal antibody production is affected by many factors related both to the antigen and the host species. For example, small molecules tend to be less immunogenic than others and can require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J Clin. Endocrinol. Metab.* 33:988–991 (1971), herein expressly incorporated by reference in its entirety.

Booster injections can be given at regular intervals, and antiserum harvested when antibody titer thereof, as determined semi-quantitatively, for example, by double immunodiffusion in agar against known concentrations of the antigen, begins to fall. (See e.g., Ouchterlony, O. et al., Chap. 19 in: *Handbook of Experimental Immunology* D. Wier (ed) Blackwell (1973), herein expressly incorporated by reference in its entirety). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology,* 2d Ed. (Rose and Friedman, Eds.) Amer. Soc.

For Microbiol., Washington, D.C. (1980), herein expressly incoprporated by reference in its entirety.

Once it can be verified that polyclonal antibodies directed to HBcAg and/or HBeAg have been generated, the mRNA obtained from the spleens of animals inoculated with HBcAg and/or HBeAg can be obtained and used as a template for the synthesis of cDNA. This cDNA, which represents (among other things) RNA encoding regions of polyclonal antibodies, can be inserted into phage that are engineered such that the cDNA insert is expressed and displayed on the surface of the phage. That is, a "phage display" cDNA library can be created from the cDNA corresponding to the MRNA encoding polyclonal antibodies that bind HBeAg and/or HBeAg. Many phage display kits that are suitable for this testing are commercially available.

Once the phage display library is obtained, a technique called "panning" is employed to isolate phage having an insert that encodes a peptide that binds HBcAg and/or HBeAg. Accordingly, HBcAg and/or HBeAg or fragments thereof are disposed on a support (e.g., a plate) and are brought in contact with the phage display library. After a sufficient time for binding has occurred, unbound phage are removed by successive washes with a isotonic buffer. Next, a plate having a bacterial lawn is brought in contact with the phage that remain bound to the plate having immobilized HBcAg and/or HBeAg. The two plates are held in position for sufficient time for infection of the bacteria and, after inoculation, the plate is incubated overnight at 37° C. The appearance of clear zones on the bacterial lawn, indicative of phage proliferation, provides evidence that the phage within the zone contain a cDNA that encodes a peptide that binds HBcAg and/or HBeAg. The DNA from such phage can be isolated, sequenced, and the protein sequence of the binding peptides can be deduced, as described above. Synthetic peptides can then be manufactured based on these sequences. Further, the cDNA inserts from positive binding phage can be subdloned into cDNA expression libraries for the production of recombinant binding partners.

Another approach to isolate molecules that bind HBcAg and/or HBeAg takes advantage of techniques developed to analyze protein/protein interactions. Conventional one and two hybrid systems, for example, can be readily adapted to identify binding partners. Such approaches include:

(1) the two-hybrid systems (Field & Song, *Nature* 340:245–246 (1989); Chien et al., *Proc. Natl. Acad. Sci.* USA 88:9578–9582 (1991); and Young K H, *Biol. Reprod.* 58:302–311 (1998), all of which are expressly incorporated by reference in their entirety);

(2) reverse two-hybrid system (Leanna & Hannink, *Nucl. Acid Res.* 24:3341–3347 (1996), herein incorporated by reference in their entirety);

(3) repressed transactivator system (Sadowski et al., U.S. Pat. No. 5,885,779), herein incorporated by reference in their entirety);

(4) phage display (Lowman HB, *Annu. Rev. Biophys. Biomol. Struct.* 26:401–424 (1997), herein incorporated by reference in their entirety); and (5) GST/HIS pull down assays, mutant operators (Granger et al., WO 98/01879) and the like (See also Mathis G., *Clin. Chem.* 41:139–147 (1995); Lam K. S. *Anticancer Drug Res.,* 12:145–167 (1997); and Phizicky et al., *Microbiol Rev.* 59:94–123 (1995), all of which are expressly incorporated by reference in their entirety).

An adaptation of the system described by Chien et al., 1991, Proc. Natl. Acad. Sci. USA, 88:9578–9582, herein incorporated by reference in its entirety, which is commercially available from Clontech (Palo Alto, Calif.) is as follows. Plasmids are constructed that encode two hybrid proteins: one plasmid consists of nucleotides encoding the DNA-binding domain of a transcription activator protein fused to a nucleotide sequence encoding HBcAg and/or HBeAg and the other plasmid consists of nucleotides encoding the transcription activator protein's activation domain fused to a cDNA encoding a candidate binding partner. The DNA-binding domain/HBcAg and/or HBeAg fusion plasmid and the candidate binding partner cDNA are transformed into a strain of the yeast *Saccharomyces cerevisiae* that contains a reporter gene (e.g., GFP or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can also be used to rapidly screen candidate binding partner libraries generated from animals for proteins that interact with the "bait" gene product (HBcAg and/or HBeAg/DNA binding domain). For example, total cDNA (representing total mRNA) generated from animals that may or may not have polyclonal antibodies specific for HBcAg and/or HBeAg can be fused to the DNA encoding an activation domain. This library and a plasmid encoding a hybrid of a bait gene encoding the HBcAg and/or HBeAg product fused to the DNA-binding domain are co-transformed into a yeast reporter strain, and the resulting transformants are screened for those that express the reporter gene.

For example, and not by way of limitation, a bait gene sequence encoding HBcAg and/or HBeAg can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA/activation domain library representative of the total mRNA from an organism that may or may not have polyclonal antibodies directed to HBcAg and/or HBeAg and an activation domain that interacts with the HBcAg and/or HBeAg/DNA binding domain fusion protein can be made using methods routinely practiced in the art. According to the particular system described herein, for example, the cDNA fragments can be inserted into a vector such that they are translationally fused to the transcriptional activation domain of GAL4. This library can be co-transformed along with the bait HBcAg and/or HBeAg gene-GAL4 fusion plasmid into a yeast strain that contains a LacZ gene driven by a promoter which contains GAL4 activation sequence. A cDNA encoded protein, fused to GAL4 transcriptional activation domain, that interacts with bait HBcAg and/or HBeAg gene product will reconstitute an active GAL4 protein and thereby drive expression of the LacZ gene. Colonies that express lacZ can be detected and the cDNA can then be purified from these strains, sequenced, and synthetic peptides corresponding to these sequences can be generated, derivatized modified, or used as templates for rational drug design. The section below describes binding partners in greater detail.

Binding partners specific for HBcAg and/or HBeAg

While the most preferred peptide embodiments are at least 13 amino acids in length, many candidate binding partners and binding partners are between about 3 amino acids and about 100 amino acids or more in length. That is, desirable candidate binding partners and binding partners are about 3–125 amino acids in length, more desirable candidate binding partners and binding partners are between about 3–100 amino acids in length, preferred candidate binding partners and binding partners are between about 3–75 amino acids in length, more preferred candidate binding partners and binding partners are between about 3–50 amino acids in length, and most preferred candidate binding partners and binding partners are between about 13–25 amino acids in length. Some embodiments, for example have the formula "$X^1_n$CKAS$X^2_n$" or "$X^1_n$CRAS$X^2_n$", wherein "$X^1$" and "$X^2$" are any amino acid and "n" is any integer, and the molecule specifically binds HBcAg and/or HBeAg. Another way of describing the molecules of this class is by the formula: "$X^1_n$CZAS$X^2_n$", wherein: "$X^1$" and "$X^2$" are any amino acid and "n" is any integer, "C" is cysteine, "Z" is lysine or arginine", "A" is alanine, and "S" is serine.

The peptides not only include those molecules containing as a primary amino acid sequence all or part of the amino acid sequence of SEQ. ID. Nos.1–78, for example, but also altered sequences in which functionally equivalent amino acid residues are substituted for residues within the sequence resulting in a silent change. Accordingly, one or more amino acid residues within the sequence of SEQ. ID. Nos. 1–78 can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The uncharged polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

Additional embodiments are nucleic acids that encode the binding partners and candidate binding partners described herein. The nucleic acid embodiments can be DNA or RNA and these molecules can be provided in constructs, plasmids, vectors, chromosomes and can be transferred to plants, virus, bacteria, insects, amphibians, reptiles, birds, animals, and mammals, including humans. Most preferably, the nucleic acid embodiments are between about 9 and about 300 nucleotides in length, although it is recognized that a fusion protein of almost any length can incorporate a nucleic acid embodiment. That is, the nucleic acid embodiments desirably have about 9–1000 nucleotides, preferably about 9–700 nucleotides, more preferably about 9–500 nucleotides, and most preferably about 9–300 nucleotides. Some nucleic acid embodiments, for example encode a peptide having the formula "$X^1{}_n CKASX^2{}_n$" or "$X^1{}_n CRASX^2{}_n$", wherein "$X^1$" and "$X^2$" are any amino acid and "n" is any integer and wherein the peptide encoded by the nucleic acid specifically binds to HBcAg and/or HBeAg. The section below describes the manufacture and use of modified and derivatized binding partners that resemble peptides (e.g., peptidomimetics) that bind HbcAg and/or HBeAg.

Modified and derivatized binding partners specific for HBcAg and/or HBeAg

The peptides described herein can be modified (e.g., the binding partners can have substituents not normally found on a peptide or the binding partners can have substituents that are normally found on the peptide but are incorporated at regions of the peptide that are not normal). The peptides can be acetylated, acylated, or aminated, for example. Substituents that can be included on the peptide so as to modify it include, but are not limited to, H, alkyl, aryl, alkenyl, alkynl, aromatic, ether, ester, unsubstituted or substituted amine, amide, halogen or unsubstituted or substituted sulfonyl or a 5 or 6 member aliphatic or aromatic ring. Thus, the term "binding partner" can refer to a modified or unmodified peptide and a chemical or a peptidomimetic that structurally (three-dimensionally or two-dimensionally) resembles a peptide that binds HBcAg and/or HBeAg.

There are many ways to make a peptidomimetic that resembles the peptides described herein. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a binding partner but that avoid the undesirable features, e.g., flexibility (loss of conformation) and bond breakdown are known as a "peptidomimetics". (See, e.g., Spatola, A. F. Chemistry and Biochemistry of Amino Acids. Peptides, and Proteins (Weistein, B, Ed.), Vol. 7, pp. 267–357, Marcel Dekker, New York (1983), which describes the use of the methylenethio bioisostere [$CH_2S$] as an amide replacement in enkephalin analogues; and Szelke et al., In peptides: Structure and Function, Proceedings of the Eighth American Peptide Symposium, (HLiruby and Rich, Eds.); pp. 579–582, Pierce Chemical Co., Rockford, Ill. (1983), which describes renin inhibitors having both the methyleneamino [$CH_2NH$] and hydroxyethylene [$CHOHCH_2$] bioisosteres at the Leu-Val amide bond in the 6–13 octapeptide derived from angiotensinogen, all of which are expressly incorporated by reference in their entireties).

In general, the design and synthesis of a peptidomimetic involves starting with the sequence of the peptide and the conformation data (e.g., geometry data, such as bond lengths and angles) of a desired peptide (e.g., the most probable simulated peptide), and using such data to determine the geometries that should be designed into the peptidomimetic. Numerous methods and techniques are known in the art for performing this step, any of which could be used. (See, e.g., Farmer, P. S., Drug Design, (Ariens, E. J. ed.), Vol. 10, pp. 119–143 (Academic Press, New York, London, Toronto, Sydney and San Francisco) (1980); Farmer, et al., in TIPS, 9/82, pp. 362–365; Verber et al., in TINS, 9/85, pp. 392–396; Kaltenbronn et al., in J. Med. Chem. 33: 838–845 (1990); and Spatola, A. F., in Chemistry and Biochemistry of Amino Acids. Peptides, and Proteins, Vol. 7, pp. 267–357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of β-sheets and α-helices in Peptides," Tibech, Vol. 8, pp. 249–255 (1990), all of which are expressly incorporated by reference in their entireties. Additional teachings can be found in U.S. Pat. Nos. 5,288,707; 5,552,534; 5,811,515; 5,817,626; 5,817,879; 5,821,231; and 5,874,529, all of which are expressly incorporated by reference in their entireties. Once the peptidomimetic is designed, it can be made using conventional techniques in peptide chemistry and/or organic chemistry.

Preferred peptidomimetics have structures that resemble a peptide whose sequence is provided in SEQ. ID. No. 1–78. While the most preferred peptidomimetics have structures that resemble peptides that are at least 13 amino acids in length, many peptidomimetics resemble peptides that are between about 3 amino acids and about 100 amino acids or more in length. That is, desirable peptidomimetics resemble peptides that are about 3–125 amino acids in length, more desirable peptidomimetics resemble peptides that are between about 3–100 amino acids in length, preferred peptidomimetics resemble peptides that are between about 3–75 amino acids in length, more preferred peptidomimetics resemble peptides that are between about 3–50 amino acids in length, and most preferred peptidomimetics resemble peptides that are between about 13–25 amino acids in length. Some embodiments, for example, are peptidomimetics that resemble a peptide having the formula "$X^1{}_n CKASX^2{}_n$" or "$X^1_n CRAS X^2_n$", wherein "$X^1$" and "$X^2$" are any amino acid and "n" is any integer, and the molecule specifically binds HBcAg and/or HBeAg. In the discussion that follows, several methods of using candidate binding partners and binding partners as templates for molecular modeling and rational drug design are described. These techniques can be applied to identify additional molecules that bind to HBcAg and/or HBeAg and thereby inhibit viral infectivity and/or modulate a host immune response.

Rational drug design approaches to identify binding partners specific for HBcAg and/or HBeAg Several methods of molecular modeling and rational drug design can be used to identify more molecules that bind to HBcAg and/or HBeAg. Rational drug design involving polypeptides requires identifying and defining a first peptide and using this first target peptide to define the requirements for a second peptide. With such requirements defined, one can find or prepare an appropriate peptide or non-peptide molecule that meets all or substantially all of the defined requirements. Thus, one goal of rational drug design is to produce structural or functional analogs of biologically active polypeptides of interest in order to fashion drugs that are, for example, more or less potent forms of a particular binding partner. (See, e.g., Hodgson, *Bio. Technology* 9:19–21 (1991)).

Combinatorial chemistry can also be used to rapidly make and test the materials constructed by rational drug design. Combinatorial chemistry is the science of synthesizing and testing compounds for bioactivity en masse, instead of one by one, the aim being to discover drugs and materials more quickly and inexpensively than was formerly possible. Many high throughput systems for rapidly testing whether a target molecule can be bound by a candidate compound are known in the art. These systems can be adapted to determine whether a candidate binding partner can interact with HBcAg and/or HBeAg or a fragment thereof.

Rational drug design and combinatorial chemistry have become more intimately related in recent years due to the development of approaches in computer-aided protein modeling and drug discovery. (See e.g., U.S. Pat. Nos. 4,908, 773; 5,884,230; 5,873,052; 5,331,573; and 5,888,738). Not only is it possible to view molecules on computer screens in three dimensions but it is also possible to examine the interactions of macromolecules such as enzymes and receptors and rationally design derivative molecules to test. (See Boorman, *Chem. Eng. News* 70:18–26 (1992)). A vast amount of user-friendly software and hardware is now available and virtually all pharmaceutical companies have computer modeling groups devoted to rational drug design. Molecular Simulations Inc., for example, sells several sophisticated programs that allow a user to start from an amino acid sequence, build a two or three-dimensional model of the protein or polypeptide, compare it to other two and three-dimensional models, and analyze the interactions of compounds, drugs, and peptides with a three dimensional model in real time.

Accordingly, in some embodiments, software is used to compare regions of binding partners with other molecules, such as peptides, peptidomimetics, and chemicals, so that therapeutic interactions can be predicted and designed. (See Schneider, *Genetic Engineering News* December: page 20 (1998), Tempczyk et al., *Molecular Simulations Inc. Solutions* April (1997) and Butenhof, Molecular Simulations Inc. Case Notes (August 1998) for a discussion of molecular modeling). For example, the protein or nucleic acid sequence of a candidate binding partner, binding partner, or a domain of these molecules can be entered onto a computer readable medium for recording and manipulation. It will be appreciated by those skilled in the art that a computer readable medium having these sequences can interface with software that converts or manipulates the sequences to obtain structural and functional information, such as protein models. That is, the functionality of a software program that converts or manipulates these sequences includes the ability to compare these sequences to other sequences or structures of molecules that are present on publicly and commercially available databases so as to conduct rational drug design.

The candidate binding partner or binding partner polypeptide or nucleic acid sequence or both can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on a computer readable medium to generate manufactures comprising the desired nucleotide or polypeptide sequence information. A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments utilize computer-based systems that contain the sequence information described herein and convert this information into other types of usable information (e.g., protein models for rational drug design). The term "a computer-based system" refers to the hardware, software, and any database used to analyze a candidate binding partner or a binding partner nucleic acid or polypeptide sequence or both, or fragments of these biomolecules so as to construct models or to conduct rational drug design. The computer-based system preferably includes the storage media described above, and a processor for accessing and manipulating the sequence data. The hardware of the computer-based systems of this embodiment comprise a central processing unit (CPU) and a database. A skilled artisan can readily appreciate that any one of the currently available computer-based systems are suitable.

In one particular embodiment, the computer system includes a processor connected to a bus that is connected to a main memory (preferably implemented as RAM) and a variety of secondary storage devices, such as a hard drive and removable medium storage device. The removable medium storage device can represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein can be inserted into the removable storage device. The computer system includes appropriate software for reading the control logic and/or the data from the removable medium storage device once inserted in the removable medium storage device. The candidate binding partner or binding partner nucleic acid or polypeptide sequence or both can be stored in a well known manner in the main memory, any of the secondary storage devices, and/or a removable storage medium. Software for accessing and processing these sequences (such as search tools, compare tools, and modeling tools etc.) reside in main memory during execution.

As used herein, "a database" refers to memory that can store a candidate binding partner or binding partner nucleotide or polypeptide sequence information, protein model information, information on other peptides, chemicals, peptidomimetics, and other agents that interact with HbcAg and/or HBeAg, and values or results from characterization assays. Additionally, a "database" refers to a memory access component that can access manufactures having recorded thereon candidate binding partner or binding partner nucleotide or polypeptide sequence information, protein model information, information on other peptides, chemicals, peptidomimetics, and other agents that interact with HbcAg and/or HBeAg, and values or results from characterization assays. The sequence data and values or results from characterization assays can be stored and manipulated in a variety of data processor programs in a variety of formats. For example, the sequence data can be stored as text in a word processing file, such as Microsoft WORD or WORDPERFECT, an ASCII file, a html file, or a pdf file in a variety of database programs familiar to those of skill in the art, such as DB2, SYBASE, or ORACLE.

A "search program" refers to one or more programs that are implemented on the computer-based system to compare a candidate binding partner or binding partner nucleotide or polypeptide sequence with other nucleotide or polypeptide sequences and other agents including but not limited to peptides, peptidomimetics, and chemicals stored within a database. A search program also refers to one or more programs that compare one or more protein models to several protein models that exist in a database and one or more protein models to several peptides, peptidomimetics, and chemicals that exist in a database. Still further, a search program can be used to compare values or results from characterization assays and agents that modulate binding partner-mediated effects on viral infectivity and/or host immune system response.

A "retrieval program" refers to one or more programs that can be implemented on the computer-based system to identify a homologous nucleic acid sequence, a homologous protein sequence, or a homologous protein model. A retrieval program can also used to identify peptides, peptidomimetics, and chemicals that interact with HBcAg and/or EBeAg or a protein model of HBcAg and/or HBeAg stored in a database. A retrieval program can also be used to obtain "a binding partner profile" that is composed of a chemical structure, nucleic acid sequence, or polypeptide sequence or model of an molecule that interacts with HBcAg and/or HBeAg and, thereby inhibits viral infectivity or modulates a host immune response to HBV.

As a starting point to rational drug design, a two or three dimensional model of a polypeptide of interest is created (e.g., a binding partner or candidate binding partner whose sequence is provided in SEQ. ID. Nos. 1–78). In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971), herein expressly incorporated by reference in its entirety. Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, 4$^{th}$ Edition, Prentice-Hall, N.J. (1972), herein expressly incorporated by reference in its entirety).

Alternatively, protein models of a polypeptide of interest can be constructed using computer-based protein modeling techniques. By one approach, the protein folding problem is solved by finding target sequences that are most compatible with profiles representing the structural environments of the residues in known three-dimensional protein structures. (See, e.g., U.S. Pat. No. 5,436,850, herein expressly incorporated by reference in its entirety). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., U.S. Pat. Nos. 5,557,535; 5,884,230; and 5,873,052, all of which are expressly incorporated by reference in their entireties). Conventional homology modeling techniques have been used routinely to build models of proteases and antibodies. (Sowdhamini et al., *Protein Engineering* 10:207, 215 (1997), herein expressly incorporated by reference in its entirety). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON that constructs a low resolution model. A full-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and organized to energy minimization using the molecular modeling package QUANTA. (See e.g., Aszódi et al., Proteins:Structure, Function, and Genetics, Supplement 1:38–42 (1997), herein expressly incorporated by reference in its entirety).

In a preferred approach, the commercially available "Insight II 98" program (Molecular Simulations Inc.) and accompanying modules are used to create a two and/or three dimensional model of a polypeptide of interest from an amino acid sequence. Insight II is a three-dimensional graphics program that can interface with several modules that perform numerous structural analysis and enable real-time rational drug design and combinatorial chemistry. Modules such as Builder, Biopolymer, Consensus, and Converter, for example, allow one to rapidly create a two dimensional or three dimensional model of a polypeptide, carbohydrate, nucleic acid, chemical or combinations of the foregoing from their sequence or structure. The modeling tools associated with Insight II support many different data file formats including Brookhaven and Cambridge databases; AMPAC/MOPAC and QCPE programs; Molecular Design Limited Molfile and SD files, Sybel Mol2 files, VRML, and Pict files.

Additionally, the techniques described above can be supplemented with techniques in molecular biology to design models of the protein of interest. For example, a known binding partner can be analyzed by an alanine scan (Wells, Methods in Enzymol. 202:390–411 (1991), herein expressly incorporated by reference in its entirety) or other types of site-directed mutagenesis analysis. In alanine scan, each amino acid residue of the binding partner is sequentially replaced by alanine in a step-wise fashion (i.e., only one alanine point mutation is incorporated per molecule starting at position #1 and proceeding through the entire molecule), and the effect of the mutation on the peptide's activity in a characterization assay is determined. Each of the amino acid residues of the peptide is analyzed in this manner and the regions important for the binding to HBcAg and/or HBeAg are determined. These functionally important regions can be recorded on a computer readable medium, stored in a database in a computer system, and a search program can be employed to generate a protein model of the functionally important regions. The example below describes a rational drug design approach that was used to identify fragments of the binding domains of mAbs that specifically bind HBcAg and/or HBeAg.

EXAMPLE 5

One approach to rational drug design involves sequential amino acid deletion of a known binding partner starting from either the amino or carboxy termini. Amino-terminal deletions of the binding partners of SEQ. ID. Nos. 5 and 17 were made and these peptide fragments were joined to a support and analyzed for the ability to bind HBcAg. By using this technique, a fine map of the peptide sequence involved in binding to HBcAg was obtained. As shown in Table 3, the HBcAg binding sequences for the peptides of SEQ. ID. Nos. 5 and 17 included KLSCKASGYIFTS (SEQ. ID. No. 45) and CRASQSVSTSSYSYMHWY (SEQ. ID. No. 54), respectively. The amino-terminal deletions of the peptide of SEQ. ID. Nos. 5 were also evaluated for the ability to inhibit binding of mAb 4-2 to HBcAg. (See Table 4). The amino-terminal deletion products of the peptide of SEQ. ID. No 5 that were most effective at inhibiting binding of mAb 4-2 were found to have at least the sequence VKLSCKASGYIFTS (SEQ. ID. No. 44), which provided evidence that the valine residue in SEQ. ID. No. 44 was intimately involved in binding of mAb4-2 to HBcAg.

TABLE 3

Mapping of the HBcAg binding sequence using support-bound amino terminal deletion peptides*

| Amino terminal deletion peptides | | OD at 490 nm |
|---|---|---|
| VKPGASVKLSCKASGYIFTS | (SEQ.ID.No.5) | 3.257 |
| KPGASVKLSCKASGYIFTS | (SEQ.ID.No.39) | 1.337 |
| PGASVKLSCKASGYIFTS | (SEQ.ID.No.40) | 1.722 |
| GASVKLSCKASGYIFTS | (SEQ.ID.No.41) | 2.863 |
| ASVKLSCKASGYIFTS | (SEQ.ID.No.42) | 3.219 |
| SVKLSCKASGYIFTS | (SEQ.ID.No.43) | 3.364 |
| VKLSCKASGYIFTS | (SEQ.ID.No.44) | 3.703 |
| KLSCKASGYIFTS | (SEQ.ID.No.45) | 3.694 |
| LSCKASGYIFTS | (SEQ.ID.No.46) | 0.565 |
| SCKASGYIFTS | (SEQ.ID.No.47) | 0.297 |
| CKASGYIFTS | (SEQ.ID.No.48) | 0.255 |
| KASGYIFTS | (SEQ.ID.No.49) | 0.237 |
| ASGYIFTS | (SEQ.ID.No.50) | 0.407 |
| SGYIFTS | (SEQ.ID.No.51) | 0.389 |
| GYIFTS | (SEQ.ID.No.52) | 0.414 |
| ISCRASQSVSTSSYSYMHWY | (SEQ. ID. NO.17) | 1.939 |
| SCRASQSVSTSSYSYMHWY | (SEQ.ID.No.53) | 1.452 |
| CRASQSVSTSSYSYMHWY | (SEQ.ID.No.54) | 1.415 |
| RASQSVSTSSYSYMHWY | (SEQ.ID.No.55) | 0.429 |
| ASQSVSTSSYSYMHWY | (SEQ.ID.No.56) | 0.324 |
| SQSVSTSSYSYMHWY | (SEQ.ID.No.57) | 0.310 |
| QSVSTSSYSYMHWY | (SEQ.ID.No.58) | 0.282 |
| SVSTSSYSYMHWY | (SEQ.ID.No.59) | 0.305 |
| VSTSSYSYMHWY | (SEQ.ID.No.60) | 0.369 |
| STSSYSYMHWY | (SEQ.ID.No.61) | 0.372 |
| TSSYSYMHWY | (SEQ.ID.No.62) | 0.317 |
| SSYSYMHWY | (SEQ.ID.No.63) | 0.311 |
| SYSYMHWY | (SEQ.ID.No.63) | 0.283 |
| YSYMHWY | (SEQ.ID.No.64) | 0.245 |
| SYMHWY | (SEQ.ID.No.65) | 0.218 |

*HBcAg was added at 5μg ml. Values are given as the OD at 490 nm. The original starting peptide has been written in bold face.

TABLE 4

Inhibition of mAb 4-2 binding to HBcAg by the amino terminal deletion peptides added prior to addition of mAb*.

| Amino terminal deletion peptides | | OD at 490 nm |
|---|---|---|
| VKPGASVKLSCKASGYIFTS | (SEQ.ID.No.5) | 0.453 |
| KPGASVKLSCKASGYIFTS | (SEQ.ID.No.39) | 0.202 |
| PGASVKLSCKASGYIFTS | (SEQ.ID.No.40) | 0.182 |
| GASVKLSCKASGYIFTS | (SEQ.ID.No.41) | 0.205 |
| ASVKLSCKASGYIFTS | (SEQ.ID.No.42) | 0.207 |
| SVKLSCKASGYIFTS | (SEQ.ID.No.43) | 0.175 |
| VKLSCKASGYIFTS | (SEQ.ID.No.44) | 0.152 |
| KLSCKASGYIFTS | (SEQ.ID.No.45) | 0.808 |
| LSCKASGYIFTS | (SEQ.ID.No.46) | 0.777 |
| SCKASGYIFTS | (SEQ.ID.No.47) | 0.784 |
| CKASGYIFTS | (SEQ.ID.No.48) | 0.851 |
| KASGYIFTS | (SEQ.ID.No.49) | 0.866 |
| ASGYIFTS | (SEQ.ID.No.50) | 0.920 |
| SGYIFTS | (SEQ.ID.No.51) | 0.887 |
| GYIFTS | (SEQ.ID.No.52) | 0.903 |

*The uninhibited control gave a mean OD at 490 nm of 0.871. The original starting peptide has been written in bold face.

Once a model or map of a binding partner is created, it can be compared to other models or maps so as to identify new members of a particular binding partner family. By starting with the amino acid sequence or protein model of a binding partner, for example, molecules having two-dimensional and/or three-dimensional homology can be rapidly identified. In one approach, a percent sequence identity can be determined by standard methods that are commonly used to compare the similarity and position of the amino acid of two polypeptides. Using a computer program such as BLAST or FASTA, two polypeptides can be aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{(total number of identical matches)}}{[\text{length of the longer sequence within the matched span} + \text{number of gaps introduced into the longer sequence in order to align the two sequences}]} \times 100$$

Accordingly, the protein sequence corresponding to a binding partner or a binding partner or a fragment or derivative of these molecules can be compared to known sequences on a protein basis. Protein sequences corresponding to a binding partner, or a binding partner or a fragment or derivative of these molecules are compared, for example, to known amino acid sequences found in Swissprot release 35, PIR release 53 and Genpept release 108 public databases using BLASTP with the parameter W=8 and allowing a maximum of 10 matches. In addition, the protein sequences are compared to publicly known amino acid sequences of Swissprot using BLASTX with the parameter E=0.001. The example below describes database searches that were performed on the identified binding partners so as to find homologous molecules that are expected to bind HBcAg and/or HBeAg.

EXAMPLE 6

To identify new candidate binding partners, the sequences of identified binding partners were used to search publicly available databases. The sequences KLSCKASGYIFTS (SEQ. ID. No. 45) and CRASQSVSTSSYSYMHWY (SEQ. ID. No. 54), obtained from mus musculus, were used to search for homologous molecules in Genebank, for example. Many sequences with a high degree of homology were found. Noticeably, the sequences uncovered in the search were mAb sequences from various species including, *Homo sapiens, Carassius auratus, Canis familiaris,* and *Caiman crocodilus*. These sequences are provided in Table 5 and the Sequence Listing (SEQ. ID. Nos. 66, 67, 68, and 69). Not only did these findings demonstrate that homology-based methods of rational drug design can yield new candidate binding partners but the data also provided evidence that HBcAg can bind naive B cells in a plurality of different species.

TABLE 5

Alignment of an HBcAg and HBeAg binding with sequences obtained from a Genbank and Swissprot search*

| Sequence identity | Sequence | | | | | Genebank/swissprot accession |
|---|---|---|---|---|---|---|
| Pept. #2 | V | K | P | G | ASVKLSCKASGY | |
| (mus musc.) | | | F | T | S (SEQ.ID.No.5) | |
| Homo sapiens | | | P | G | A SVRISCKASGY | P80421 |
| | | | A | F | (SEQ. ID. No. 66) | |
| Carassius auratus | K | P | G | D | SLRLSCKASGY | P19180 |
| | | | T | F | S (SEQ. ID. No. 67) | |
| Canis familiaris | V | K | P | G | G SLRLSC V ASGF | P01785 |
| | | | F | S | S (SEQ.ID.No.68) | |
| Caiman crocodilus | K | P | G | D | SLRLSCKGSGF | P03981 |
| | | | F | S | N (SEQ. ID. No. 69) | |

*The homology search was made prior to December 11, 1999.

In another embodiment, computer modeling and the sequence-to-structure-to-function paradigm is exploited to identify more binding partners and candidate binding partners. By this approach, first the structure of a binding partner or a candidate binding partner having a known response in a characterization assay is determined from its sequence using a threading algorithm, which aligns the sequence to the best matching structure in a structural database. Next, the peptide's active site (i.e., the site important for a desired response in the characterization assay) is identified and a "fuzzy functional form" (FFF)—a three-dimensional descriptor of the active site of a protein—is created. (See e.g., Fetrow et al., *J. Mol. Biol.* 282:703–711 (1998) and Fetrow and Skolnick, *J. Mol. Biol.* 281: 949–968 (1998), herein expressly incorporated by reference in its entirety). The mapping techniques described above can be used to facilitate description of the active site of the peptide.

The FFFs are built by iteratively superimposing the protein geometries from a series of functionally related proteins with known structures. The FFFs are not overly specific, however, and the degree to which the descriptors can be relaxed is explored. In essence, conserved and functionally important residues for a desired response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained. The ability to search three-dimensional structure databases for structural similarity to a protein of interest can also be accomplished by employing the Insight II using modules such as Biopolymer, Binding Site Analysis, and Profiles-3D.

By using this computational protocol, genome sequence data bases such as maintained by various organizations can be rapidly screened for specific protein active sites and for identification of the residues at those active sites that resemble a desired molecule. Several other groups have developed databases of short sequence patterns or motifs designed to identify a given function or activity of a protein. Many of these databases, notably Prosite, Blocks, Prints, the Molecular Modelling Database (MMDB), and the Protein Data Bank can use short stretches of sequence information to identify sequence patterns that are specific for a given function; thus they avoid the problems arising from the necessity of matching entire sequences.

By a similar approach, a binding partner can be identified and manufactured as follows. First, a molecular model of one or more binding partners are created using one of the techniques discussed above or as known in the art. Next, chemical libraries and databases are searched for molecules similar in structure to the known molecule. That is, a search can be made of a three dimensional data base for non-peptide (organic) structures (e.g., non-peptide analogs) having three dimensional similarity to the known structure of the target compound. See, e.g., the Cambridge Crystal Structure Data Base, Crystallographic Data Center, Lensfield Road, Cambridge, CB2 1EW, England; and Allen, F. H., et al., *Acta Crystallogr.*, B35: 2331–2339 (1979), all of which are expressly incorporated by reference in their entireties. One program that allows for such analysis is Insight II having the Ludi module. Further, the Ludi/ACD module allows a user access to over 65,000 commercially available drug candidates (MDL's Available Chemicals Directory) and provides the ability to screen these compounds for interactions with HBcAg and/or HBeAg on the computer. The identified candidate binding partners can then be analyzed in a characterization assay and new molecules can be modeled after the candidate binding partners that produce a desirable response. By cycling in this fashion, libraries of molecules that interact HBcAg and/or HBeAg and produce a desirable or optimal response in a characterization assay can be selected.

It is noted that search algorithms for three dimensional data base comparisons are available in the literature. See, e.g., Cooper, et al., *J. Comput.-Aided Mol. Design*, 3: 253–259 (1989) and references cited therein; Brent, et al.,*J. Comput.-Aided Mol. Design*, 2: 311–310 (1988) and references cited therein, all of which are expressly incorporated by reference in their entireties. Commercial software for such searches is also available from vendors such as Day Light Information Systems, Inc., Irvine, Calif. 92714, and Molecular Design Limited, 2132 Faralton Drive, San Leandro, Calif. 94577. The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the protein:protein interactions.

Alternatively, these methods can be used to identify improved binding partners from an already known binding partner. The composition of the known binding partner can be modified and the structural effects of modification can be determined using the experimental and computer modeling methods described above. The altered structure can be compared to the active site structure of HBcAg and/or HBeAg to determine if an improved fit or interaction results. In this manner systematic variations in composition, such as by varying side groups, can be quickly evaluated to obtain modified binding partners of improved specificity or activity.

Additionally, a computer model of HBcAg and/or HBeAg can be obtained using the approaches described above, and this model can be compared with libraries of candidate binding partners in real time. For example, a search program can locate several structures within the database that have a given set of molecular properties, which correspond to the constraints provided by the HBcAg and/or HBeAg model. With the aid of computer graphics and a retrieval program, candidate binding partners can be obtained from the database, modeled, and evaluated for the ability to interact with HBcAg and/or HBeAg. This approach is referred to as a "computer generated binding assay". Such assays can be performed in the presence or absence of competing molecules.

A number of articles review computer modelling of drugs interactive with specific-proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090, all of which are expressly incorporated by reference in their entireties. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario).

Many more computer programs and databases can be used with embodiments to identify candidate binding partners and binding partners that inhibit viral infectivity and/or modulate a host immune system response. The following list is intended not to limit the invention but to provide guidance to programs and databases that are useful with the approaches discussed above. The programs and databases that can be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990), herein incorporated by reference), FASTA (Pearson and Lipman, *Proc. Natl. Acad. Sci. USA*, 85: 2444 (1988), herein incorporated by reference), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), Biopendium (Inpharmatica), SBdBase (Structural Bioinformatics), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure.

Although the peptides described above can effectively modulate an immune response to HBV in a subject, binding partner-fusion proteins can be created to take advantage of already existing highly potent immune responses in a subject. That is, peptides that bind HBcAg and/or HBeAg can be fused with molecules, which are known to elicit a potent immune response in a subject. In this manner, high titer antibodies present in the subject are redirected to HBcAg and/or HBeAg and, thus, HBV can more effectively be cleared from the subject. These binding partner-fuision proteins are referred to as "specificity exchangers" and the section below describes their manufacture and use in detail.

Binding partner specificity exchangers

Antibodies can be redirected to new antigens using bi-functional synthetic peptides called binding partner-fusion proteins or specificity exchangers. (See Sällberg et al., *Biochemical & Biophysical Research Communications*, 205:1386–90 (1994) and U.S. Pat. No. 5,869,232, both disclosures are herein incorporated by reference in their entireties). One portion of the specificity exchanger, referred to as the "specificity domain", comprises a molecule that resembles an antibody binding domain or fragment thereof, which binds a desired molecule (e.g., HBcAg and/or BBeAg) and another portion of the specificity exchanger, called the "antigenic domain", serves as an antigen for antibody recognition (preferably recognition by a high titer antibody). The specificity domain can be a binding partner itself (e.g., peptide, peptidomimetic, or chemical) that resembles a binding domain of an antibody or fragment thereof; whereas, the antigenic domain can comprise molecules including, but not limited to, carbohydrates, lipids, proteins, and nucleic acids that have epitopes, which are rrecognized by antibodies present in an animal.

Any of the approaches used to identify and characterize binding partners described herein can be used to manufacture the specificity domains of a specificity exchanger specific for HBV. Preferably, the antigenic domain comprises an epitope found on a pathogen (e.g., bacteria, mold, fungus, or virus) or a toxin (e.g., pertussis toxin or cholera toxin) or a non-self antigen. The specificity domain and the antigenic domain can be directly joined or indirectly joined. For example, in some embodiments, specificity exchangers comprise linkers (e.g., λ linkers or biotin-avidin linkers) between the specificity and antigenic domains so as to encourage greater flexibility and better performance. The specificity exchangers are desirably analyzed in the characterization assays described above or in modified characterization assays as will be apparent to one of skill in the art provided the description herein. The example below describes the manufacture of specificity exchangers having a specificity domain directed to HBcAg and/or HBeAg and an antigenic domain directed to an anti-HSV mAb.

EXAMPLE 7

An approach to manufacture specificity exchangers that can redirect high titer antibodies to HBV is provided in this example. A first set of specificity exchangers having a specificity domain containing the HBcAg binding sequence KLSCKASGYIFTS (SEQ. ID. No. 45) and a C terminal antigenic domain containing the epitope for a monoclonal antibody directed to the herpes simplex virus type 1 gG2 (HSV gG2) protein was created. A second set of specificity exchangers having a specificity domain containing the HBcAg binding sequence VKLSCKASGYIFTS (SEQ. ID. No. 44) and a C-terminal antigenic domain containing the epitope for a monoclonal antibody directed to the HSV gG2 protein was also constructed. The sequences of these binding partner fusion proteins are provided in the Sequence Listing (SEQ. ID. Nos. 70–76). These molecules were made by conventional peptide synthesis.

Once candidate binding partners have been identified, desirably, they are analyzed in a characterization assay. Further cycles of modeling and characterization assays can be employed to more narrowly define the parameters needed in a binding partner. Each binding partner and its response in a characterization assay can be recorded on a computer readable media and a database or library of binding partners and respective responses in a characterization assay can be generated. These databases or libraries can be used by researchers to identify important differences between active and inactive molecules so that compound libraries are enriched for binding partners that have favorable characteristics. The section below describes several binding partner characterization assays that can be used to evaluate candidate binding partners.

Binding Partner and Candidate binding partner characterization assays

The evaluation of candidate binding partners and, thus, the determination whether a candidate binding partner is, in fact, a binding partner can be accomplished by using a "characterization assay". The term "characterization assay" refers to an assay, experiment, or analysis made on a candidate binding partner or binding partner, which evaluates the ability of said candidate binding partner or binding partner to interact with HBcAg and/or HBeAg or fragments thereof, effect viral infection, and a host immune system response. Encompassed by the term "characterization assay" are binding studies (e.g., enzyme immunoassays (EIA), enzyme-linked immunoassays (ELISA), competitive binding assays, computer generated binding assays, support bound binding studies, and one and two hybrid systems), infectivity studies (e.g., reduction of viral infection, propagation, attachment to a host cell), and analysis of host immune system response e.g., (clearance of viral particles, reduction in viral lode, activation of antigen presenting cells, and effect on B and T cell presentation). In general, the characterization assays can be described in three general catagories; (1) assays that determine whether a candidate binding partner binds to HBcAg and/or HBeAg; (2) assays that determine whether a binding partner reduces viral infectivity; and (3) assays that determine whether a binding partner modulates a host immune system response.

Preferred HBcAg and/or HBeAg binding assays use multimeric agents. One form of multimeric agent concerns a manufacture comprising a candidate binding partner or binding partner, or fragments thereof disposed on a support. Another form of multimeric agent involves a manufacture comprising HBcAg and or HBeAg or fragments thereof disposed on a support. These multimeric agents provide the attached molecule in such a form or in such a way that a sufficient affinity is achieved. A "support" can be a termed a carrier, a protein, a resin, a cell membrane, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. A candidate binding partner or binding partner can also be joined to inorganic supports, such as silicon oxide material (e.g. silica gel, zeolite, diatomaceous earth or aminated glass) by, for example, a covalent linkage through a hydroxy, carboxy, or amino group and a reactive group on the support.

In some multimeric agents, the macromolecular support has a hydrophobic surface that interacts with a portion of the candidate binding partner, binding partner, or viral antigen (e.g., HBcAg and/or HBeAg) by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, candidate binding partner, binding partner, or viral antigen can be covalently bound to supports including proteins and oligo/polysaccharides (e.g. cellulose, starch, glycogen, chitosane or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the candidate binding partner or binding partner or fragments thereof. For example, cyanogen bromide activated matrices, epoxy activated matrices, thio and thiopropyl gels, nitrophenyl chloroformate and N-hydroxy succinimide chlorformate linkages, or oxirane acrylic supports can be used. (Sigma).

Furthermore, in some embodiments, a liposome or lipid bilayer (natural or synthetic) is contemplated as a support and a candidate binding partner, binding partner, or viral antigen can be attached to the membrane surface or are incorporated into the membrane by techniques in liposome engineering. By one approach, liposome multimeric supports comprise a candidate binding partner, binding partner, or viral antigen that is exposed on the surface. A hydrophobic domain can be joined to the candidate binding partner or binding partner so as to facilitate the interaction with the membrane.

Supports for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, and Chromosorbe® (Johns-Manville Products, Denver Colo.). Ligand conjugated Chromosorbe® (Synsorb-Pk) has been tested in humans for the prevention of hemolytic-uremic syndrome and was reported as not presenting adverse reactions. (Armstrong et al. *J. Infectious Diseases* 171:1042–1045 (1995)). For some embodiments, a "naked" carrier (i.e., lacking an attached binding partner) that has the capacity to attach a binding partner in the body of a organism is administered. By this approach, a "prodrug-type" therapy is envisioned in which the naked carrier is administered separately from the binding partner and, once both are in the body of the organism, the carrier and the binding partner are assembled into a multimeric complex.

The insertion of linkers, such as linkers (e.g., "λ linkers" engineered to resemble the flexible regions of λ phage) of an appropriate length between the candidate binding partner, binding partner, or viral antigen and the support are also contemplated so as to encourage greater flexibility of the candidate binding partner, binding partner, or viral antigen and thereby overcome any steric hindrance that can be presented by the support. The determination of an appropriate length of linker that allows for optimal binding to HBcAg and/or HBeAg, inhibition of viral infectivity, and modulation of host immune response can be determined by screening the attached molecule with varying linkers in the characterization assays detailed in the present disclosure.

A composite support comprising more than one type of binding partner is also envisioned. A "composite support" can be a carrier, a resin, or any macromolecular structure used to attach or immobilize two or more different binding partners. In some embodiments, a liposome or lipid bilayer (natural or synthetic) is contemplated for use in constructing a composite support or binding partners are attached to the membrane surface or are incorporated into the membrane using techniques in liposome engineering.

As above, the insertion of linkers, such as λ linkers, of an appropriate length between the binding partner and the support is also contemplated so as to encourage greater flexibility in the molecule and thereby overcome any steric hindrance that can occur. The determination of an appropriate length of linker that allows for optimal binding to HBcAg and/or HBeAg, inhibition of viral infectivity, and modulation of host immune response or lack thereof, can be determined by screening the binding partners with varying linkers in the characterization assays detailed in the present disclosure.

Several approaches to identify agents that interact with HBcAg and/or HBeAg, employ a multimeric support having candidate binding partner, binding partner, or HBcAg and/or HBeAg or a fragment thereof. For example, support-bound candidate binding partner can be contacted with "free" HBcAg and/or HBeAg and an association can be determined directly (e.g., by using labeled HBcAg and/or HBeAg) or indirectly (e.g., by using a labeled antibody directed to the HBcAg and/or BBeAg). Thus, candidate binding partners are identified as binding partners by virtue of the association of HBcAg and/or HBeAg with the support-bound candidate binding partner. Alternatively, support-bound HBcAg and/or HBeAg can be contacted with "free" candidate binding partner and the amount of associated candidate binding partner can be determined directly (e.g., by using labeled binding partner) or indirectly (e.g., by using a labeled antibody directed to the binding partner).

Assays that determine whether a candidate binding partner binds to HBcAg and/or HBeAg can be conducted in a variety of formats. Most simply, techniques in immunology can be employed or readily adapted to ascertain whether a candidate binding partner has bound HBcAg and/or HBeAg. In one set of characterization assays, the interaction of 20 amino acid long candidate binding partners with HBcAg was determined by enzyme immunoassays (EIA), as described in the example below.

EXAMPLE 8

To determine whether a candidate binding partner bound to HBcAg and/or HbeAg, a multimeric support-based binding assay was performed. Accordingly, synthetic peptides corresponding to the VH and VL domains of the sequenced mAbs were passively adsorbed to 96 well microplates in serial dilutions starting at 200 μg/ml. The peptide coated plates were then incubated with HBcAg and HBeAg serially diluted in PBS-GT. The amount of HBcAg and HBeAg bound by the peptides was then detected using a mAb directed to an epitope common to HBcAg and HBeAg lSee Sällberg et al., *J General Virology* 74:1335–1340 (1993), herein expressly incorportaed by reference in its entirety) diluted 1:3000 in PBS-GT. The quantity of bound mAb was determined by addition by peroxidase labeled rabbit anti-mouse IgG (P260, Dako AS, Denmark). The plates were developed by incubation with ortho-phenylene-diamine (Sigma) and the absorbance at 492 nm was evaluated.

As shown in Table 6, many peptides were found to bind to HBcAg in this characterization assay. Two conserved domains were found in five of the binding partners (SEQ. ID. Nos. 5, 16, 17, 28, and 29), which bound HBcAg with high affinity. These conserved domains were Cys-Lys-Ala-Ser (SEQ. ID. No. 77) and Cys-Arg-Ala-Ser (SEQ. ID. No. 78). Taken together, the levels of affinity of the five binding partners and the conservation of the two domains provided evidence that these domains are intimately involved in binding to HBcAg.

concentrations as low as 0.67 $\mu$g/ml. The converse of an aspect of this experiment was also performed. That is, various dilutions of support-bound binding partners (SEQ. ID. Nos. 5, 16, 17, 28, and 29) were contacted with 10 $\mu$g/ml of HBcAg and binding was evaluated. As shown in Table 8, the peptides of SEQ. ID. Nos. 5, 16, 17, and 28 showed

TABLE 6

Binding of support-bound peptides to HBcAg and NS3

| Peptide # | Sequence of peptide | | HBcAg 2 $\mu$g/well | HBcAg 0.2 $\mu$g/well | HCV NS3 |
|---|---|---|---|---|---|
| MAb 4-2 | | | | | |
| 1 | VKLQQSGTEVVKPGASVKLS | (SEQ.ID.No.4) | 0.323 | 0.124 | 0.021 |
| 2 | VKPGASVKLSCKASGYIFTS | (SEQ.ID.No.5) | 3.692 | 1.146 | 0.269 |
| 3 | CKASGYIFTSYDIDWVRQTP | (SEQ.ID.No.6) | 0.525 | 0.187 | 0.032 |
| 4 | YDIDWVRQTPEQGLEWIGWI | (SEQ.ID.No.7) | 0.551 | 0.202 | 0.089 |
| 5 | EQGLEWIGWIFPGEGSTEYN | (SEQ.ID.No.8) | 0.706 | 0.256 | 0.182 |
| 6 | FPGEGSTEYNEKFKGRATLS | (SEQ.ID.No.9) | 0.325 | 0.121 | 0.109 |
| 7 | EKFKGRATLSVDKSSSTAYM | (SEQ.ID.No.10) | 0.883 | 0.194 | 0.035 |
| 8 | VDKSSSTAYMELTRLTSEDS | (SEQ.ID.No.11) | 0.363 | 0.134 | 0.041 |
| 9 | ELTRLTSEDSAVYFCARGDY | (SEQ.ID.No.12) | 0.574 | 0.195 | 0.073 |
| 10 | AVYFCARGDYDYYRRYFDLW | (SEQ.ID.No.13) | 0.981 | 0.304 | 0.038 |
| 11 | DYYRRYFDLWGQGTTVTVS | (SEQ.ID.No.14) | 0.356 | 0.133 | 0.022 |
| MAb 5H7 | | | | | |
| 12 | DJVLTQSPASLAVSLGQRAT | (SEQ.ID.No.15) | 0.53 | 0.156 | 0.025 |
| 13 | LAVSLGQRATISCRASQSVS | (SEQ.ID.No.16) | 3.113 | 0.807 | 0.128 |
| 14 | ISCRASQSVSTSSYSYMHWY | (SEQ.ID.No.17) | 2.475 | 0.449 | 0.156 |
| 15 | TSSYSYMHWYQQKPGQPPKL | (SEQ.ID.No.18) | 1.442 | 0.574 | 0.028 |
| 16 | QQKPGQPPKLLIKYASNLES | (SEQ.ID.No.19) | 0.299 | 0.064 | 0.016 |
| 17 | LIKYASNLESGVPARFSGSG | (SEQ.ID.No.20) | 0.357 | 0.112 | 0.020 |
| 18 | GVPARFSGSGSGTDFTLNIH | (SEQ.ID.No.21) | 0.409 | 0.141 | 0.027 |
| 19 | SGTDFTLNIHPVEEEDTATY | (SEQ.ID.No.22) | 0.649 | 0.205 | 0.206 |
| 20 | PVEEEDTATYYCQHSWEIPY | (SEQ.ID.No.23) | 0.625 | 0.207 | 0.124 |
| 21 | YCQHSWEIPYTFGGGTKLEI | (SEQ.ID.No.24) | 0.498 | 0.173 | 0.052 |
| 22 | TFGGGTKLEIKKADAAPAV | (SEQ.ID.No.25) | 0.273 | 0.084 | 0.024 |
| 23 | KRADAAPAVSIFPPSSKLG | (SEQ.ID.No.26) | 0.465 | 0.162 | 0.021 |
| MAb9C8 | | | | | |
| 24 | IQLQQSGAELVKPGASVKIS | (SEQ.ID.No.27) | 0.369 | 0.123 | 0.021 |
| 25 | VKPGASVKISCKASGYSFTG | (SEQ.ID.No.28) | 3.129 | 0.845 | 0.097 |
| 26 | CKASGYSFTGYNMNWVKQSH | (SEQ.ID.No.29) | 2.29 | 0.356 | 0.053 |
| 27 | YNMNWVKQSHGKSLEWIGNI | (SEQ.ID.No.30) | 0.157 | 0.114 | 0.021 |
| 28 | GKSLEWIGNINPYYGSTSYN | (SEQ.ID.No.31) | 0.289 | 0.114 | 0.028 |
| 29 | NPYYGSTSYNQKFKGKATLT | (SEQ.ID.No.32) | 0.783 | 0.213 | 0.021 |
| 30 | QKFKGKATLTVDKSSSTAYM | (SEQ.ID.No.33) | 1.115 | 0.207 | 0.035 |
| 31 | VDKSSSTAYMQLNSLTSEDS | (SEQ.ID.No.34) | 0.338 | 0.114 | 0.106 |
| 32 | QLNSLTSEDSAVYYCARGKG | (SEQ.ID.No.35) | 0.528 | 0.121 | 0.035 |
| 33 | AVYYCARGKGTGFAYWGQGT | (SEQ.ID.No.36) | 1.203 | 0.227 | 0.035 |
| 34 | GFAYWGQGTLVTVSAAKTT | (SEQ.ID.No.37) | 0.898 | 0.192 | 0.035 |
| 35 | LVTVSAAKPPSVYPLVPV | (SEQ.ID.No.38) | 0.59 | 0.198 | 0.032 |

The five "high affinity" binding partners (SEQ. ID. Nos. 5, 16, 17, 28, and 29) were also bound to a support and were analyzed for the ability to bind various dilutions of "free" HBcAg and HBeAg. As shown in Table 7, the five peptides exhibited appreciable binding to HBcAg and HBeAg at appreciable binding at low concentrations of HBcAg and/or HBeAg. In each of these experiments, the amount of peptide binding was directly proportional to the amount of HBcAg or HBeAg added or the amount of peptide disposed on the support.

TABLE 7

Binding of dilutions of HBcAg and HBeAg to support-bound peptides

| Peptide # | Amount HBcAg added ($\mu$g/ml) | | | | | | Amount HBeAg added ($\mu$g/ml) | | | | | |
|---|---|---|---|---|---|---|---|---|---|---|---|---|
| | 20 | 10 | 5 | 2.5 | 1.25 | 0.67 | 20 | 10 | 5 | 2.5 | 1.25 | 0.67 |
| 2 | 3.453 | 1.692 | 0.989 | 0.374 | 0.155 | 0.034 | 0.751 | 0.222 | 0.096 | 0.063 | 0.043 | 0.081 |
| 13 | 2.635 | 0.872 | 0.501 | 0.195 | 0.079 | 0.028 | 0.393 | 0.060 | 0.038 | 0.030 | 0.023 | 0.024 |

TABLE 7-continued

Binding of dilutions of HBcAg and HBeAg to support-bound peptides

| Peptide # | Amount HBcAg added (μg/ml) | | | | | | Amount HBeAg added (μg/ml) | | | | | |
|---|---|---|---|---|---|---|---|---|---|---|---|---|
| | 20 | 10 | 5 | 2.5 | 1.25 | 0.67 | 20 | 10 | 5 | 2.5 | 1.25 | 0.67 |
| 14 | 2.660 | 1.150 | 0.633 | 0.252 | 0.117 | 0.039 | 0.687 | 0.246 | 0.132 | 0.102 | 0.056 | 0.046 |
| 25 | 2.652 | 0.897 | 0.359 | 0.159 | 0.058 | 0.036 | 0.319 | 0.096 | 0.050 | 0.115 | 0.034 | 0.022 |
| 26 | 1.479 | 0.601 | 0.245 | 0.101 | 0.038 | 0.028 | 0.241 | 0.091 | 0.091 | 0.063 | 0.026 | 0.027 |
| 27 | 0.305 | 0.115 | 0.059 | 0.042 | 0.026 | 0.020 | 0.040 | 0.037 | 0.029 | 0.032 | 0.021 | 0.018 |

TABLE 8

Binding of 10 μg/ml HBcAg to dilutions of support-bound peptides

| Peptide # | Amount peptide coated (μg/ml) | | | | | |
|---|---|---|---|---|---|---|
| | 100 | 50 | 25 | 12.5 | 6.25 | 3.125 |
| 2 | 1.453 | 1.218 | 1.039 | 0.913 | 0.597 | 0.333 |
| 13 | 0.900 | 0.434 | 0.276 | 0.240 | 0.388 | 0.355 |
| 14 | 0.641 | 0.569 | 0.636 | 0.514 | 0.630 | 0.413 |
| 25 | 1.011 | 0.766 | 0.569 | 0.423 | 0.298 | 0.217 |
| 26 | 0.422 | 0.198 | 0.181 | 0.179 | 0.156 | 0.171 |
| 27 | 0.151 | 0.170 | 0.162 | 0.181 | 0.175 | 0.168 |

Variations of the characterization assays described above include competitive binding assays. For example, the five high affinity peptides (SEQ. ID. Nos. 5, 16, 17, 28, and 29) were analyzed for the ability to prevent binding of mnAb 4-2 to HBcAg. Initial experiments were conducted by contacting binding partner to HBcAg prior to introducing the antibody. As shown in Table 9, all five high affinity binding partners were able to inhibit binding of mAb 4-2 when the concentration of peptide was raised to 200 μg/ml. The peptides of SEQ. ID. Nos. 5, 28, and 29 effectively reduced binding of the antibody at concentrations as low as 100 μg/ml and the peptides of SEQ. ID. No. 5 and 29 appreciably reduced binding of mAb 4-2 at concentrations as low as 50 μg/ml. The ability of the five high affinity binding partners to compete for binding of the mAb 4-2 to HBeAg was also analyzed. When the peptides of SEQ. ID. Nos. 5, 16, 28, and 29 were provided at 200 μg/ml in the presence of mAb 4-2, the binding of the antibody to HBcAg was significantly inhibited. (See Table 10). Similarly, the peptides of SEQ. ID. Nos. 5, 16, 28, and 29 effectively competed with mAb 4-2 at 100 μg/ml. The peptide of SEQ. ID. No. 28 prevented binding of mAb 4-2 at a concentration as low as 12.5 μg/ml, whereas, the peptides of SEQ. ID. Nos. 5 and 16 prevented binding of mAb 4-2 at 6.25 μg/ml.

TABLE 9

Inhibition of mAb 4-2 binding to HBcAg coated at 1 μg/ml by prior incubation with synthetic peptides*.

| Peptide | Amount peptide (μg/ml) added prior to mAb 4-2 | | | | | |
|---|---|---|---|---|---|---|
| # | 200 | 100 | 50 | 25 | 12.5 | 6.25 |
| 2 | 0.078 | 0.083 | 0.188 | 0.341 | 0.331 | 0.336 |
| 13 | 0.299 | 0.345 | 0.364 | 0.429 | 0.365 | 0.350 |
| 14 | 0.305 | 0.370 | 0.402 | 0.439 | 0.380 | 0.370 |
| 25 | 0.173 | 0.274 | 0.312 | 0.359 | 0.339 | 0.329 |

TABLE 9-continued

Inhibition of mAb 4-2 binding to HBcAg coated at 1 μg/ml by prior incubation with synthetic peptides*.

| Peptide | Amount peptide (μg/ml) added prior to mAb 4-2 | | | | | |
|---|---|---|---|---|---|---|
| # | 200 | 100 | 50 | 25 | 12.5 | 6.25 |
| 26 | 0.201 | 0.280 | 0.337 | 0.383 | 0.357 | 0.351 |
| 16 | 0.368 | 0.394 | 0.383 | 0.406 | 0.391 | 0.336 |

*Values have been given as the OD at 490 nm. 100% binding of mAb without addition of peptide corresponds to an mean OD of 0.379

TABLE 10

Inhibition of mAb 4-2 binding to HBcAg coated at 5 μg/ml by simultaneous addition of mAb and synthetic peptides*.

| Peptide | Amount peptide (μg/ml) added simultaneous as mAb 4-2 | | | | | |
|---|---|---|---|---|---|---|
| # | 200 | 100 | 50 | 25 | 12.5 | 6.25 |
| 2 | 0.139 | 0.194 | 0.395 | 0.698 | 0.824 | 0.867 |
| 13 | 0.859 | 0.891 | 0.998 | 1.027 | 1.037 | 0.979 |
| 14 | 1.468 | 1.458 | 1.557 | 1.390 | 1.442 | 1.264 |
| 25 | 0.302 | 0.910 | 1.217 | 1.200 | 1.207 | 1.178 |
| 26 | 0.341 | 0.947 | 1.250 | 1.347 | 1.275 | 1.196 |
| 16 | 0.925 | 1.115 | 1.232 | 1.239 | 1.235 | 1.065 |

*Values have been given as the OD at 490 nm. 100% binding of mAb without addition of peptide corresponds to an mean OD of 1.229

Preferably, the specificity exchangers are also evaluated in characterization assays. Some of these characterization assays evaluate the ability of the specificity exchanger to interact with the target molecule and the redirecting antibody. Other characterization assays evaluate the ability of the specificity exchanger to fix complement. Still more characterization assays are designed to determine whether a specificity exchanger can bind to the target molecule, bind to the redirecting antibody, and fix complement. The example below describes several characterization assays that were conducted on the specificity exchangers.

EXAMPLE 9

To evaluate the efficacy of the specificity exchangers described above, several binding assays using a mAb specific for HSV gG2 were conducted. In one assay, the various specificity exchangers were coated onto microtiterplates and were bound with the mAb specific for HSV gG2. As shown in Table 11, the specificity exchangers provided in SEQ. ID. Nos. 71, 74, and 75 appreciably bound the mAb. In another assay, HBcAg was coated onto microtiter plates, specificity exchanger was added (20 μg/well), and the binding of the mAb specific for HSV gG2 was determined. The specificity exchangers provided in SEQ. ID. Nos. 71 and 74 appreciably bound the immobilized HBcAg and allowed for the binding of the mAb specific for HSV gG2. In another binding assay, HBeAg was coated onto microtiter plates, specificity exchanger was added (20 μg/well), and the binding of the mAb specific for HSV gG2 was determined. Similarly, the specificity exchangers provided in SEQ. ID. Nos. 71 and 74 appreciably bound the immobilized HBeAg and allowed for the binding of the mAb specific for HSV gG2. These results demonstrate that specificity exchangers specific for HBcAg and/or HBeAg can be manufactured and used to redirect HBV to high titer antibodies. The characterization assays used to evaluate binding partners can also be used and/or modified for the analysis of the specificity exchangers.

TABLE 11

Redirection of antibodies specific for an epitope within HSV gG2

| | | gG2 mAb binding to indicated antigen on solid phase | | |
|---|---|---|---|---|
| | | fusion peptide | HBcAg | HBeAg |
| | | Addition of fusion peptide in solution (20 μg/well) | | |
| Peptide | | | | |
| # | Fusion peptide sequence | no | yes | yes |
| 13 | KLSCKASGYIFTSEHRGGPEE (SEQ. ID. No. 70) | 0.040 | 0.020 | 0.022 |
| 14 | KLSCKASGYIFTSHRGGPEEF (SEQ. ID. No. 71) | 1.622 | 0.550 | 0.638 |
| 15 | KLSCKASGYIFTSRGGPEEFE (SEQ. ID. No. 72) | 0.062 | 0.016 | 0.040 |
| 16 | VKLSCKASGYIFTSEHRGGPE (SEQ. ID. No. 73) | 0.060 | 0.038 | 0.029 |
| 17 | VKLSCKASGYIFTSHRGGPEE (SEQ. ID. No. 74) | 0.884 | 1.462 | 1.727 |
| 18 | VKLSCKASGYIFTSHRGGPEE (SEQ. ID. No. 75) | 0.213 | 0.037 | 0.032 |
| 19 | VKLSCKASGYIFTSGGPEEFE (SEQ. ID. No. 76) | 0.018 | 0.025 | 0.024 |
| Neg ctrl | Peptide 16 | Not tested | 0.038 | 0.022 |

To demonstrate that the biological activities encompassed by the Fc domain of the HSV mAb was introduced to the specificity exchanger (SEQ. ID. No. 74), a complement binding assay was performed. Accordingly, the assay was conducted by mixing the antibody to be tested with the appropriate antigen and allowing binding to occur overnight. Subsequently, rabbit complement, which is consumed if the antibody binds the antigen and the complement, was added. To determine the amount of residual complement in the mixture, sheep erythrocytes and an antibody to sheep erythrocytes was added. If the complement has been exhausted (i.e. a complement binding antibody has bound to the antigen) lysis of red blood cells will not occur. If no antibody-antigen complex has formed then the remaining complement will lyse the red blood cells bound by the specific antibody.

The complement binding of the HBcAg-specific mAb 9C8 was evaluated together with the ability of the specificity exchanger peptide (SEQ. ID. No. 74) to inhibit the binding of mAb 9C8 to HBcAg. Serial dilutions of mAb 9C8 were mixed with HBcAg in the presence and absence of the specificity exchanger peptide (SEQ. ID. No. 74). As shown in Table 12, the mAb 9C8 bound to HBcAg appreciably bound complement and the specificity exchanger peptide (SEQ. ID. No. 74) was unable to compete away bound mAb 9C8.

TABLE 12

Complement binding activity of mAb 9C8 in the presence of a specificity exchanger

| Amount peptide SEQ. ID. No. 74 | Amount HBcAg | Amout mAb 9C8 (pmol) | | | |
|---|---|---|---|---|---|
| (pmol) | (pmol) | 6.7 | 3.3 | 1.7 | 0.8 |
| none | none | − | − | − | − |
| none | 24 | + | + | − | − |
| 4000 | 24 | + | + | + | − |
| 400 | 24 | + | + | − | ? |
| 40 | 24 | + | + | − | − |
| 4 | 24 | + | + | − | − |
| 0.4 | 24 | + | + | − | − |

The complement binding of mAb 4-2 was also evaluated in conjunction with the ability of the specificity exchanger peptide (SEQ. ID. No. 74) to inhibit binding of mAb 4-2 to HBcAg. Accordingly, serial dilutions of mAb 4-2 were mixed with HBcAg in the presence and absence of the specificity exchanger peptide (SEQ. ID. No. 74). As shown in Table 13, the mAb 4-2 bound to HBcAg also bound complement. Further, the specificity exchanger (SEQ. ID. No. 74) appreciably inhibited the binding of mAb 4-2 to HBcAg.

TABLE 13

Complement binding activity of mAb 4-2 in the presence of a specificity exchanger

| Amout peptide SEQ. ID. No. 74 | Amount HBcAg | Amout 4-2 mAb (pmol) | | | |
|---|---|---|---|---|---|
| (pmol) | (pmol) | 6.7 | 3.3 | 1.7 | 0.8 |
| none | none | − | − | − | − |
| none | 24 | +/− | + | − | − |
| 4000 | 24 | − | − | − | − |
| 400 | 24 | − | − | − | − |
| 40 | 24 | − | − | − | − |
| 4 | 24 | +/− | − | − | +/− |
| 0.4 | 24 | +/− | +/− | − | − |

The ability of the complex of HSV mAb, specificity exchanger (SEQ. ID. No. 74), and HBcAg to bind complement was also evaluated. Accordingly, serial dilutions of the HSV mAb were mixed with HBcAg in the presence and absence of the specificity exchanger (SEQ. ID. No. 74). As shown in Table 14, the HSV niAb did not activate complement in the absence of the specificity exchanger (SEQ. ID. No. 74). However, when the HSV mAb and the specificity exchanger (SEQ. ID. No. 74) were present at equimolar ratios, the HSV mAb bound BBeAg through the specificity exchanger (SEQ. ID. No. 74) and the mAb-specificity exchanger-HBcAg complex was able to bind complement. (See Table 15). These data confirm that an antibody bound to the specificity exchanger (SEQ. ID. No. 74) can impart the biological activity of the antibody to the specificity exchanger peptide.

TABLE 14

Complement binding activity of a specificity exchanger bound to HBcAg and a HSV mAb

| Amout peptide | Amount | Amout HSV mAb (pmol) | | | | | | | |
|---|---|---|---|---|---|---|---|---|---|
| SEQ. ID. No. 74 (pmol) | HBcAg (pmol) | 6.7 | Excess peptide | 3.3 | Excess peptide | 1.7 | Excess peptide | 0.8 | Excess peptide |
| none | none | – | | – | | – | | – | |
| None | 24 | – | | – | | – | | – | |
| 4000 | 24 | +/– | 597 | – | 1212 | – | 2352 | – | 5000 |
| 400 | 24 | – | 59.7 | – | 121.2 | – | 235.2 | + | 500 |
| 40 | 24 | – | 5.97 | – | 12.12 | – | 23.52 | – | 50 |
| 4 | 24 | – | 0.597 | +/– | 1.212 | + | 2.352 | – | 5 |
| 0.4 | 24 | – | 0.0597 | – | 0.1212 | +/– | 0.2352 | – | 0.5 |

In another type of characterization assay, the ability of a binding partner to inhibit viral infectivity is analyzed. Several types of HBV viral infectivity assays can determine the efficacy of anti-HBV materials by detecting a reduction in HBV nucleic acid synthesis and/or the presence of HBV antigens. These assays can be readily adapted to determine whether a binding partner inhibits HBV propagation. By one approach, a human hepatoblastoma cell culture assay is used to evaluate the ability of binding partners to inhibit HBV replication. (See Korba and Gerin, *Antiviral Res.* 19: 55–70 (1992) and Korba and Milman, *Antiviral Res.* 15:217–228 (1991), both references herein incorporated by reference in their entirety). By another approach, persistently infected HepG2 cells can be used to evaluate the ability of binding partners to inhibit HBV replication. The toxicity of binding partners can also be assessed under the same culture and treatment conditions. The example below describes several characterization assays that can be used to determine the ability of a binding partner to inhibit HBV infectivity.

EXAMPLE 10

A human hepatoblastoma cell culture assay can be used to evaluate the ability of a binding partner to inhibit HBV replication. The detection of HBV propagation is determined by analyzing the presence of HBV nucleic acid in the media and cells. Human hepatoblastoma 2.2.15 cells are grown to confluency and are provided a daily dose of binding partner in RPMI1640 medium with 2% fetal bovine serum. Ideally, a titration of binding partner (e.g., 500 $\mu$M to 1 $\mu$M) is provided to aliquots of cells. As a control, scrambled peptides having a similar amino acid content are added at the same concentrations. Medium is analyzed for HBV virion DNA before treatment and daily during treatment. HBV DNA can be extracted from medium and analyzed by slot blot analysis, for example. Intracellular HBV DNA is also analyzed after 10 days of treatment. Preferably, the cellular DNA is prepared and analyzed by Southern blot analysis using a $^{32}$P-labelled 3.2 kb EcoRI HBV DNA fragment as a probe. Quantitation can be accomplished by comparison to HBV standards loaded on each gel. Desirable binding partners will inhibit HBV propagation by greater than 50%, as demonstrated by a reduction of HBV virion DNA in the medium and 3.2 Kb DNA syntheses.

Additionally, the effect of a binding partner on HBV propagation in HEP-G2 cells can be monitored by detecting the presence of HBV antigens (e.g., HBsAg and HBeAg) in the media. Kits that detect these hepatitis markers are commercially available. (Abbott Laboratories). As above, human hepatoblastoma 2.2.15 cells are grown to confluency and are provided a daily dose (200 $\mu$g/ml) of binding partner in RPMI1640 medium with 2% fetal bovine serum. Medium is assayed for HBV virion DNA before treatment and periodically during treatment for the presence of a viral antigen by using a commercially available kit (Abbott Laboratories). Desirable binding partners will inhibit HBV propagation by greater than 50%, as demonstrated by a reduction of viral antigen present in the medium.

By another approach, HEP-G2 cells, persistently infected with HBV, are treated daily with fresh D-MEM containing 20% FBS and a titration of binding partner, as above. After 9 days incubation and treatment, the cells and overlay medium are harvested separately to assay the quantity of nucleic acids. Extracellular virion DNA in untreated cells will range from from 50 to 150 pg/ml in the overlay medium. Intracellular HBV DNA replication intermediates (RI) in untreated cells will range from 50 to 100 pg/$\mu$g cell DNA. Hybridization analysis will show that approximately 1 pg intracellular HBV DNA/$\mu$g cellular DNA to 2–3 genomic copies per cell and 1.0 pg of extracellular HBV DNA/ml overlay medium to $3\times10^3$ viral particles/ml. HBV RNA can also be analyzed by Northern blot hybridization analysis using a $^{32}$P-labeled 3.2 Kb gel-purified cloned genomic probe. Quantitive analysis of intracellular HBV DNA and 14BV RNA can be performed using an AMBIS beta scanner. Desirable binding partners will inhibit the level of HBV propagation demonstrated by untreated cells by a value of greater than 50%, as demonstrated by a reduction of virion replication intermediates (RI) and 3.2 Kb DNA syntheses.

Additionally, the effect of a binding partner on HBV propagation in a human hepatoblastoma cell culture assay is monitored by detecting the presence of HBV antigens (e.g., HBsAg and HBeAg) in the media. Kits that detect these hepatitis markers are commercially available. (Abbott Laboratories). HEP-G2 cells are persistently infected with HBV and are treated daily with fresh D-MEM containing 20% FBS and 200 $\mu$g/ml binding partner. After 9 days of incubation and treatment, the overlay medium is harvested to assay the quantity of HBsAg and HBeAg by EIA (Abbott Laboratories). The overlay medium is diluted to levels of antigen in the linear range of the assay. Standard curves using dilutions of positive HBsAg and HBeAg controls are included in each assay. Desirable binding partners will inhibit HBV propagation by greater than 50%, as demonstrated by a reduction of viral antigen present in the medium.

Toxicity of a binding partner can also be determined by the exclusion of neutral red dye uptake in cells grown in 96-well plates and treated as described above. One day after the final addition of binding partner, medium is removed and 0.2 ml of DPBS containing 0.01% neutral red dye (Sigma, Inc.) is added to each well. Cells are allowed to recover for two hours. Dye is removed, cells are washed with DPBS and then 0.2 ml of 50% EtOH/1% glacial acetic acid is added to each well. After 30 minutes of gentle mixing, absorbance at 510 nm is measured and compared to untreated control cultures. Desirable binding partners will demonstrate a toxicity of less than 5% at concentrations ten fold greater than that shown to be effective at inhibiting HBV propagation. The in vitro assays described in this example can be used to rapidly determine whether a binding partner can inhibit HBV infection.

Characterization assays also include experiments designed to test binding partners in vivo. There are many animal models that are suitable for evaluating the ability of a binding partner to inhibit HBV infection. The woodchuck model has been used in hepatitis research for over a decade. (See e.g., Gerin, J. L. 1984. In Advances in Hepatitis Research. F. Chisari, ed. Masson Publishing USA, Inc. New York, pp. 40–48; Gerin et al. 1986 In Vaccines 86: New approaches to Immunization. F. Brown et al., eds. Cold Spring Harbor Laboratory Press, N.Y., pg 383–386, herein expressly incorporated by reference in its entirety). The woodchuck hepatitis virus (WHV) is closely related to HBV, both immunologically and in terms of sequence homology. Woodchucks are now bred and reared for experimental hepatitis research. Infection of young animals with defined WHV inocula yields chronic carriers for drug testing and research. At least one commercial testing facility is devoted to testing of compounds in woodchucks. Tennant, B. C. and J. L. Gerin. 1994. In The Liver: Biology and Pathobiology, Third Edition. I. M. Arias et al., eds. Raven Press, Ltd., N.Y. pp 1455–1466, herein expressly incorporated by reference in its entirety. Because of the sequence homology between HBV and WHV, the efficacy of the binding partners can be evaluated in the woodchuck model. Furthermore, demonstration of binding partner efficacy in this model is a clear demonstration of a specific pharmacologic effect to those of skill in the art.

A more recently developed animal model for HBV uses transgenic rats that express human hepatitis B virus genes. (See e.g., Takahashi et al., *Proc. Natl. Acad. Sci. U.S.A.* 92, 1470–1474 (1995), herein expressly incorporated by reference in its entirety). These animals develop acute hepatitis and viral particles and HBeAg are seen in the blood between three and seven days after transfection. HBV is expressed in the liver and liver cell death results. These effects and the subsequent clearing of virions from the blood mimic the effects of acute HBV infection in humans. Therefore activity of binding partners in this model is indicative of therapeutic activity in humans to those of skill in the art.

Chimpanzees are hosts for HBV, and therefore constitute another animal model for HBV induced disease. The serological events following infection in chimpanzees are identical to that observed in humans. Both acute and chronic infections result from exposure of chimpanzees to HBV. However, chimpanzees do not have recognizable clinical symptoms of hepatitis. Cornelius, C. E., 1988, in The Liver: Biology and Pathobiology, Second Ed. I. M. Arias et al., eds. Raven Press, Ltd., N.Y., pp. 1315–1336, herein expressly incorporated by reference in its entirety. Demonstration of activity in this model, in which the animal is infected with the same virus that infects humans, is also indicative of therapeutic effect in humans to those skilled in the art. The example below describes in vivo assays that can be performed in woodchucks to determine whether a binding partner can inhibit HBV infection.

EXAMPLE 11

Binding partners can be evaluated for their ability to inhibit HBV infection at a commercial facility, which routinely screens anti-HBV and anti-hepatocellular carcinoma drug candidates in the woodchuck hepatitis model. (Marmotech, Inc. of Ithaca, N.Y.). Two doses of binding partner are tested, 20 mg/kg and 2 mg/kg, with three animals receiving each dose. Binding partners are administered intravenously in 0.1 ml of PBS every other day for 30 days, for a total of 15 doses. The primary end point of the assay is level of circulating virus. Blood samples are collected on day 0, prior to drug treatment, and at days 1, 2, 4, 8, 15, 22 and 30 of treatment. Virus is quantitated by dot blot or Southern blot analysis using the methods described above or by monitoring the presence of viral antigens in the blood using a commercially available kit (Abbott Laboratories). Alternatively, binding partners can be evaluated in rats or mice made transgenic for HBV genes. (See Takahashi et al., *Proc. Natl. Acad. Sci. U.S.A.*, 92:1470–1474 (1995), herein incorporated by reference in its entirety). The next example describes an approach that was used to evaluate the efficacy of a binding partner (e.g., a specificity exchanger) for use as the active ingredient in a pharmaceutical that is administered to treat or prevent HBV infection.

EXAMPLE 12

By using an animal model of HBV infection, the therapeutic efficacy of a specificity exchanger directed to HBV was determined. In a first group of experiments, two HBeAg-transgenic mice (obtained from Dr. David R Milich, The Scripps Research Institute, La Jolla, Calif.) were injected i.p. with 500 μl of undiluted hybridoma supernatants. The mice were then bled on day zero, two, six and nine post-injection. Sera were then tested for the change in serum HBeAg levels as determined by EIA (Sorin Biomedica, Saluggia, Italy). As shown in Table 15, neither PBS or mAb 3–4 had an effect on the HBeAg levels in serum. In contrast, mAb 4-2 complexed an appreciable amount of serum HBeAg (i.e., over a two fold increase in serum HBeAg was detected by EIA). This data confirms that mAb 4-2 binds HBeAg in vivo at an epitope that does not compete with the antibodies present in the commercial EIA.

TABLE 15

In vivo aggregation of serum HBeAg in transgenic mice by mAbs 3-4 and 4-2*

| Mab given in vivo | Fold change in serum HBeAg levels as determined by EIA in HBeAg-Tg mice at indicated day from injection: 0 | 2 | 6 | 9 |
|---|---|---|---|---|
| PBS | 1 | 0.8 | 1.1 | 1 |
| 3-4 | 1 | 0.8 | 1.1 | 1.1 |
| 4-2 | 1 | 2.7 | 2.2 | 1.7 |

*Mabs were injected i.p. as 0.5 ml culture supernatants containing around 10 μg/ml of mAb (~30 pmole/mouse).

In a second group of experiments, two HBeAg-transgenic mice were injected ip. with either culture media (RPMI), the HSV mAb, the HBcAg-specific mAb 9C8, or the specificity exchanger peptide (SEQ. ID. No. 74). As shown in Table 16, the negative controls RPMI and the HSV mAb alone show only a 1.2 to 1.9 fold changes in aggregation of serum HBeAg. By day nine, the mice that received the specificity exchanger peptide (SEQ. ID. No. 74) had a 3.3 fold increase in aggregation of serum HBeAg levels. Similar to the 4-2 mAb, the specificity exchanger peptide (SEQ. ID. No. 74) retained the ability to complex serum HBeAg in vivo. These results verify that a specificity exchanger directed to an HBV antigen can be created and that such an agent can appreciably aggregate HBcAg and/or HBeAg in vivo.

TABLE 16

In vivo aggregation of serum HBeAg in transgenic mice*

| mAb given in vivo | Fold change in serum HBeAg levels as determined by EIA in HBeAg-Tg mice at indicated day from injection | | | | |
|---|---|---|---|---|---|
| Day | 0 | 1 | 3 | 6 | 9 |
| RPMI | 1 | 1.2 | 1.7 | 1.4 | 1.7 |
| HSV mAb | 1 | 1.2 | 1.9 | 1.5 | 1.7 |
| 9C8 | 1 | 1.4 | 2.0 | 1.7 | 1.8 |
| Peptide of SEQ. ID. No. 74 | 1 | 1.5 | 2.3 | 2.3 | 3.3 |

*Mabs were injected i.p. as 0.2 to 0.5 ml culture supernatants containing approx. 10 μg/ml of mAb (~30 pmole/mouse). The final volume injected per mouse was 0.5 ml.

Another particularly desirable characterization assay evaluates specificity exchangers in chimpanzees infected with HBV. The next example describes this characterization assay in detail.

EXAMPLE 13

An approach to evaluate the efficacy of a specificity exchanger in chimpanzees sis provided below. Accordingly, chimpanzees are repeatedly inoculated with an antigen that is known to promote a high titer antibody response (e.g., HSVgG2). After the course of immunization, the presence of polyclonal antibodies to the antigen is verified. Subsequently, the chimpanzee is infected with HBV and after a stable infection is verified, the infected animal is provided a therapeutically effective dose of the specificity exchanger (SEQ. ID. No. 74). The dosages used in various animals include 100 μg/kg body weight to 500 μg/kg body weight. Aggregation of HBcAg and/or HBeAg is verified and the clearance of viral particles and long term monitoring of infection is conducted by analyzing blood samples for the presence of HBV nucleic acid or protein by using the techniques described in Example 10. Over a period of several treatments with the specificity exchanger, a reduction in viral lode will be observed.

Characterization assays also include experiments that evaluate the ability of a binding partner to modulate a host immune response to HBV. It is contemplated that HBV reduces the CTL response of an infected host by targeting HBcAg to a high number of B cells, which then process the antigen. Through antigen leakage, HBcAg-peptides are present on the class I molecules of B cells whereby the CTL response against HBcAg and HBV is inhibited. To prevent this molecular cascade and, thereby, modulate a host immune response to HBV, binding partners that inhibit the binding of HBcAg to B cells can be provided so as to prevent tolerization of the HBcAg-specific CTL response of an infected host. Subjects infected with HBV have antigen presenting cells (e.g., dendritic cells and B cells) that display HBV viral antigens and effect T cell proliferation. By analyzing the ability of binding partners to modulate B cell presentation of HBV antigens in vitro, for example, one can accurately determine whether a binding partner will modulate a host immune response to HBV. Accordingly, this type of characterization assay is performed by obtaining "naïve" B cells (i.e., B cells from animals that have not come in contact with HBV or an HBV antigen) and contacting the naïve B cells with "experienced" T cells (i.e., T cells from animals that have been immunized with a HBV viral antigen or infected with HBV) in the presence of a binding agent. The ability of the binding agent to modulate a host immune response to HBV is then determined by monitoring the production of cytokines and/or T cell proliferation. The example below describes an assay that was used to determine the ability of a binding partner to modulate an immune response in a subject.

EXAMPLE 14

A characterization assay that was used to evaluate the ability of a binding partner to modulate a host immune system response to HBV was conducted as follows. Groups of Balb/c mice were immunized subcutaneously with 20 μg HBcAg. Ten days later, draining lymph nodes were harvested and experienced CD4$^+$T cells were purified using anti-CD4 coated magnetic beads (Dynal AS, Oslo, Norway) according to the manufacturers instructions. Naïve B cells were obtained from syngeneic mice, which had not been immunized. These B cells were used as antigen presenting cells in the characterization assay.

The ability of the different mAbs and peptides to block B cell uptake and antigen presentation of HBcAg-peptides to HBcAg-specific CD4+ T cells was then tested in vitro. The cell populations were mixed at a B/T cell ratio of 1:5 and added at a final concentration of approximately $2.5 \times 10^5$ to $5.0 \times 10^5$ cells per well in a 96 well microplate. Approximately, 20 μg of HBcAg was preincubated with the binding partner. The binding partner mixtures were then added to the cells and the plates were incubated for 26 to 96 hours at 37° C. The effect of the binding partners on T cell proliferation was determined by monitoring [$^3$H] thymidine incorporation.

As shown in Table 17, mAb 4-2 and the HBcAg and HBeAg binding peptide (SEQ.ID. No. 74) inhibited B cell mediated antigen presentation of HBcAg to specific CD4+ T cells. In contrast, the control peptide (SEQ.ID. No. 19) showed no inhibition. Thus, the specificity exchanger (SEQ.ID. No. 74) not only bound HBcAg and HBeAg but also possessed the ability to block uptake and antigen presentation of HBcAg by B cells.

TABLE 17

Inhibition of B cell-mediated antigen presentation of HBcAg to experienced T cells*

| Cell population | Antigen | Inhibitor | cpm | SD | % inhibition* of APC |
|---|---|---|---|---|---|
| T cells | 20 μg HBCAg | none | 82 | 30 | Negative control |
| T + B cells | none | none | 110 | 46 | background proliferation |
| T + B cells | 20 μg HBcAg | none | 573 | 28 | Positive control |
| T + B cells | 20 μg HBcAg | MAb 4-2 | 245 | 123 | 71 |
| T + B cells | 20 μg HBcAg | 4-2 peptide (SEQ. ID. No. 74) | 345 | 8 | 49 |
| T + B cells | 20 μg HBcAg | Control peptide (SEQ. ID. No. 19) | 572 | 183 | 0 |

*Calculated as 1 minus [(cpm of cells with inhibitor minus cpm of background proliferation) divided by (positive control cpm minus cpm of background proliferation)].

It is contemplated that some binding partners will be highly efficient B cell stimulatory molecules in that they effect a rapid and potent T cell response. Other binding partners are contemplated to weakly activate antigen presenting cells and, thus, stimulate a weak T cell response, if any at all. Classes of such weak and strong binding partners can be created based on similarities in structure and function. These classes and profiles can be entered onto a computer readable media, placed in a database, and accessed for comparison so as to develop more effective weak and strong binding partners. The section below describes the use of binding partners as biotechnological tools and diagnostic reagents.

Biotechnological tools and diagnostic reagents

In one aspect, binding partners are used as biotechnological tools that detect the presence or absence, as well as the concentration of HBcAg or HBeAg in a biological sample. The peptides can be used in many different immunohistochemical techniques including but not limited to, immunoprecipitation, Western blot, affinity purification, and in situ analysis. Advantageously, some embodiments can be used as high affinity probes that detect HBV in tissues that are difficult to label using conventional antibodies.

Desirably, the binding partners are used as diagnostic reagents to determine the presence of HBV infection in a subject or to monitor the treatment of HBV infection in a subject. Further, the manufacture of kits that incorporate the binding partners are contemplated. The detection component of these kits will typically be supplied in combination with one or more of the following reagents. A support capable of absorbing or otherwise binding protein will often be supplied. Available supports include membranes of nitrocellulose, nylon or derivatized nylon that can be characterized by bearing an array of positively charged substituents. One or more control reagents, buffers, enzymes, and detection material (e.g., radioisotope, enzyme conjugate and substrate, magnetic particle, gold particle, or secondary antibody with or without conjugate) can be supplied in these kits.

The presence of HBV in a protein sample can be detected by using conventional assays and a binding partner or specificity exchanger. In some embodiments, a binding partner or specificity exchanger is used to immunoprecipitate HBV viral antigens from solution or are used to react with HBV viral antigens on Western or Immunoblots. Favored diagnostic embodiments also include enzyme-linked immunosorbant assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference. Other embodiments employ aspects of the immune-strip technology disclosed in U.S. Pat. Nos. 5,290,678; 5,604,105; 5,710,008; 5,744,358; and 5,747,274, herein incorporated by reference.

In another preferred protein-based diagnostic, binding partners or specificity exchangers are attached to a support in an ordered array, wherein a plurality of binding partners or specificity exchangers are attached to distinct regions of the support that do not overlap with each other. These arrays are designed to be "addressable" such that the distinct locations are recorded and can be accessed as part of an assay procedure. The binding partners or specificity exchangers (collectively referred to as "probes" in this context) are joined to the support in different known locations. The knowledge of the precise location of each probe makes these "addressable" arrays particularly useful in binding assays. For example, an addressable array can comprise a support having several regions to which are joined a plurality of probes that specifically recognize the presence of HBcAg and/or HBeAg in a biological sample obtained from subjects suspected of having contact with HBV.

Accordingly, proteins are recovered from biological samples from subjects suspected of contracting HBV and are labeled by conventional approaches (e.g., radioactivity, colorimetrically, or fluorescently). The labeled protein samples are then applied to the array under conditions that permit binding to the probes. If a protein in the sample binds to a probe on the array, then a signal will be detected at a position on the support that corresponds to the location of the probe-protein complex. Since the identity of each labeled sample is known and the region of the support on which the labeled sample was applied is known, an identification of the presence of HBV infection can be rapidly determined. These approaches are easily automated using technology known to those of skill in the art of high throughput diagnostic analysis.

In another embodiment, an opposite approach to that presented above can be employed. Proteins present in biological samples can be disposed on a support so as to create an addressable array. Preferably, the protein samples are disposed on the support at known positions that do not overlap. The presence of a viral antigen in each sample is then determined by applying labeled probes that recognize HBcAg and/or HBeAg. Because the identity of the biological sample and its position on the array is known, an identification of the presence of HBV infection can be rapidly determined. As detailed above, any addressable array technology known in the art can be employed with this aspect and display the protein arrays on the chips in an attempt to maximize antibody binding patterns and diagnostic information.

Although many embodiments were chemically synthesized using conventional techniques in peptide chemistry, nucleic acids encoding the peptides can be introduced into cells in vitro or in vivo and the recipient cells can be made to express a binding partner, preferably a specificity exchanger. A description of several approaches to make cells that express a binding partner is given in the section below.

Cells made to express binding partners

Cells made to express a binding partner, whether in vivo or in vitro, are embodiments of the invention. The concentration of a binding partner, preferably a specificity exchanger, can be raised in a cell in vitro by transfecting expression constructs encoding these molecules. In vivo expression constructs can also be used to deliver a nucleic acid encoding a binding partner to liver cells in an animal. Liposome mediated transfer can also be used to transfer a nucleic acid encoding a binding partner to a cell in vivo or in vitro.

The following is provided as one possible method to express a binding partner or specificity exchanger in a cell in vitro. First, the methionine initiation codon for a binding partner or specificity exchanger and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the nucleic acid lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). The vector pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding the polypeptide to be expressed can be obtained by PCR from a bacterial vector having the binding partner using oligonucleotide primers complementary to the nucleic acid and containing restriction endonuclease sequences for Pst I incorporated into the 5' primer and BglII at the 5' end of the corresponding cDNA 3' primer, taking care to ensure that the nucleic acid is positioned in frame with the poly A signal. The purified fragment obtained from the resulting PCR reaction is digested with PstI, blunt ended with an exonuclease, digested with BglII, purified and ligated to pXT1, now containing a poly A signal and digested with BglII. The ligated product is transfected into a suitable cell line using Lipofectin (Life Technologies, Inc., Grand Island, N.Y.) under conditions outlined in the product specification. Positive transfectants are selected after growing the transfected cells in 600 $\mu$g/ml G418 (Sigma, St. Louis, Mo.). Preferably the expressed protein is released into the culture medium, thereby facilitating purification.

Another approach utilizes the "Xpress system for expression and purification" (Invitrogen, San Diego, Cailf.). The Xpress system is designed for high-level production and purification of recombinant proteins from bacterial, mammalian, and insect cells. The Xpress vectors produce recombinant proteins fused to a short N-terminal leader peptide that has a high affinity for divalent cations. Using a nickel-chelating resin (Invitrogen), the recombinant protein can be purified in one step and the leader can be subsequently removed by cleavage with enterokinase.

One preferred vector for the expression of binding partners and fragments of binding partner is the pBlueBacHis2 Xpress. The pBlueBacHis2 Xpress vector is a Baculovirus expression vector containing a multiple cloning site, an ampicillin resistance gene, and a Lac Z gene. By one approach, the binding partner or specificity exchanger nucleic acid is cloned into the pBlueBacHis2 Xpress vector and SF9 cells are infected. The expression protein is then isolated or purified according to the manufacturer's instructions. Several other cultured cell lines having recombinant constructs or vectors comprising a binding partner or specificity exchanger are embodiments and their manufacture would be routine given the present disclosure.

By similar approaches, a nucleic acid encoding a binding partner can be incorporated into a vector that expresses the binding partner or specificity exchanger in liver cells in vivo. (Huber et al. *Proc. Natl. Acad. Sci. USA* 88:8039–8043 (1991), herein expressly incorporated by reference in its entirety. Many such organ specific vectors have been described in the literature and nucleic acids encoding a binding partner or specificity exchanger can be incorporated into these vectors by conventional techniques in molecular biology. (See U.S. Pat. Nos. 5,981,274; 5,998,205; and 6,025,195, all of which are herein incorporated by reference in their entirety.) In the disclosure below, several pharmaceutical embodiments are described.

Pharmaceutical preparations and methods of administration

Binding partners, preferably a specificity exchanger, are suitable for incorporation into pharmaceuticals for administration to subjects in need of a compound that treats or prevents HBV infection. These pharmacologically active compounds can be processed in accordance with conventional methods of galenic pharmacy to produce medicinal agents for administration to mammals including humans. The active ingredients can be incorporated into a pharmaceutical product with and without modification. Further, the manufacture of pharmaceuticals or therapeutic agents that deliver the pharmacologically active compounds of this invention by several routes are aspects. For example, and not by way of limitation, DNA, RNA, and viral vectors having sequence encoding a binding partner or specificity exchanger are used with embodiments. Nucleic acids encoding a binding partner or specificity exchanger can be administered alone or in combination with other active ingredients.

The compounds can be employed in admixture with conventional excipients, i.e., pharmaceutically acceptable organic or inorganic carrier substances suitable for parenteral, enteral (e.g., oral) or topical application that do not deleteriously react with the pharmacologically active ingredients described herein. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable vehicles are described in Remmington's Pharmaceutical Sciences, 15th Edition, Easton:Mack Publishing Company, pages 1405–1412 and 1461–1487(1975) and The National Formulary XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular pharmaceutical formulation having a binding partner or specificity exchanger can vary based on the individual needs of the patient and the treatment or preventative measure sought. Therapeutic efficacy and toxicity of such compounds can be determined by standard pharmaceutical procedures in cell cultures or experimental animals, e.g., ED50 (the dose therapeutically effective in 50% of the population). For example, a binding partner or specificity exchanger can be evaluated using the characterization assays described above. The data obtained from these assays is then used in formulating a range of dosage for use with other organisms, including humans. The dosage of such compounds lies preferably within a range of circulating concentrations that include the ED50 with no toxicity. The dosage varies within this range depending upon type of binding partner or specificity exchanger, the dosage form employed, sensitivity of the organism, and the route of administration.

Normal dosage amounts of a binding partner or specificity exchanger can vary from approximately 1 to 100,000 micrograms, up to a total dose of about 10 grams, depending upon the route of administration. Desirable dosages include about 250 $\mu$g-1 mg, about 50 mg–200 mg, and about 250 mg–500 mg.

In some embodiments, the dose of a binding partner or specificity exchanger preferably produces a tissue or blood concentration or both from approximately 0.1 $\mu$M to 500 mM. Desirable doses produce a tissue or blood concentration or both of about 1 to 800 $\mu$M. Preferable doses produce a tissue or blood concentration of greater than about 10 μM to about 500 μM. Although doses that produce a tissue concentration of greater than 800 μM are not preferred, they can be used with some embodiments. A constant infusion of a binding partner or specificity exchanger can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease, age of the organism, and weight or size of the organism; diet, time and frequency of administration, drug combination(s), reaction sensitivities, and tolerance/response to therapy. Short acting pharmaceutical compositions are administered daily or more frequently whereas long acting pharmaceutical compositions are administered every 2 or more days, once a week, or once every two weeks or even less frequently.

Routes of administration of the pharmaceuticals include, but are not limited to, topical, transdermal, parenteral, gastrointestinal, transbronchial, and transalveolar. Transdermal administration is accomplished by application of a cream, rinse, gel, etc. capable of allowing the pharmacologically active compounds to penetrate the skin. Parenteral routes of administration include, but are not limited to, electrical or direct sinjection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having pharmacologically active compounds described herein that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein incorporated by reference.

Compositions having pharmacologically active compounds that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having pharmacologically active compounds that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the pharmacologically active compounds.

Compositions having pharmacologically active compounds that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment. Once the pharmaceutical comprising the binding partner or specificity exchanger has been obtained, it can be administered to a organism in need to treat or prevent HBV infection.

Aspects of the invention also include a coating for medical equipment such as prosthetics, implants, and instruments. Coatings suitable for use in medical devices can be provided by a gel or powder containing the binding partners or by polymeric coating into which a binding partner is suspended. Suitable polymeric materials for coatings or devices are those that are physiologically acceptable and through which a therapeutically effective amount of the binding partner can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al. that is incorporated herein by reference in its entirety.

In several aspects, a pharmaceutical having a binding partner, preferably a specificity exchanger, is provided to a subject in need of an agent that treats or prevents HBV infection. These pharmaceuticals can be formulated with or without a carrier or other agent in addition to the active ingredient, as described above. Methods to formulate such pharmaceuticals that inhibit HBV infection and/or modulate a host immune response to HBV are embodiments.

Other embodiments involve methods to treat or prevent HBV infection. Accordingly, a subject in need of a binding partner or specificity exchanger that inhibits HBV infection and/or modulates a host immune response to HBV is provided a therapeutically effective amount of a pharmaceutical having said binding partner or specificity exchanger. Such subjects in need can include individuals at risk of contracting HBV or are already afflicted with HBV. These individuals can be identified by clinical or biochemical techniques.

Although the invention has been described with reference to embodiments and examples, it should be understood that various modifications can be made without departing from the spirit. Accordingly, the invention is limited only by the following claims. All references cited herein are hereby expressly incorporated by reference.

What is claimed is:

1. An isolated or purified peptide comprising a sequence selected from the group consisting of SEQ ID NO:6, SEQ ID NO:13, SEQ ID NO:36, and SEQ ID NO:37.

2. The peptide of claim 1, wherein said sequence is SEQ ID NO:6.

3. The peptide of claim 1, wherein said sequence is SEQ ID NO:13.

4. The peptide of claim 1, wherein said sequence is SEQ ID NO:36.

5. The peptide of claim 1, wherein said sequence is SEQ ID NO:37.

6. An isolated or purified peptide consisting of a sequence selected from the group consisting of SEQ ID NO:5, SEQ ID NO:6, SEQ ID NO:13, SEQ ID NO:16, SEQ ID NO:28, SEQ ID NO:29, SEQ ID NO:33, SEQ ID NO:36, and SEQ ID NO:37.

7. The peptide of claim 6, wherein said sequence is SEQ ID NO:5.

8. The peptide of claim 6, wherein said sequence is SEQ ID NO:6.

9. The peptide of claim 6, wherein said sequence is SEQ ID NO:13.

10. The peptide of claim 6, wherein said sequence is SEQ ID NO:16.

11. The peptide of claim 6, wherein said sequence is SEQ ID NO:28.

12. The peptide of claim 6, wherein said sequence is SEQ ID NO:29.

13. The peptide of claim 6, wherein said sequence is SEQ ID NO:33.

14. The peptide of claim 6, wherein said sequence is SEQ ID NO:36.

15. The peptide of claim 6, wherein said sequence is SEQ ID NO:37.

* * * * *

SEQUENCE LISTING

```
<160> NUMBER OF SEQ ID NOS: 78

<210> SEQ ID NO 1
<211> LENGTH: 119
<212> TYPE: PRT
```

<213> ORGANISM: Artificial Sequence
<220> FEATURE:
<223> OTHER INFORMATION: Artificial Oligonucleotide

<400> SEQUENCE: 1

```
Val Lys Leu Gln Gln Ser Gly Thr Glu Val Lys Pro Gly Ala Ser
 1               5                  10                  15

Val Lys Leu Ser Cys Lys Ala Ser Gly Tyr Ile Phe Thr Ser Tyr Asp
                20                  25                  30

Ile Asp Trp Val Arg Gln Thr Pro Glu Gln Gly Leu Glu Trp Ile Gly
                35                  40                  45

Trp Ile Phe Pro Gly Glu Gly Ser Thr Glu Tyr Asn Glu Lys Phe Lys
            50                  55                  60

Gly Arg Ala Thr Leu Ser Val Asp Lys Ser Ser Ser Thr Ala Tyr Met
 65                  70                  75                  80

Glu Leu Thr Arg Leu Thr Ser Glu Asp Ser Ala Val Tyr Phe Cys Ala
                    85                  90                  95

Arg Gly Asp Tyr Asp Tyr Tyr Arg Arg Tyr Phe Asp Leu Trp Gly Gln
                100                 105                 110

Gly Thr Thr Val Thr Val Ser
            115
```

<210> SEQ ID NO 2
<211> LENGTH: 129
<212> TYPE: PRT
<213> ORGANISM: Artificial Sequence
<220> FEATURE:
<223> OTHER INFORMATION: Artificial Oligonucleotide

<400> SEQUENCE: 2

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Gln Ser Val Ser Thr Ser
                20                  25                  30

Ser Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                    85                  90                  95

Glu Ile Pro Tyr Thr Phe Gly Gly Gly Thr Lys Leu Glu Ile Lys Arg
                100                 105                 110

Ala Asp Ala Ala Pro Ala Val Ser Ile Phe Pro Pro Ser Ser Lys Leu
            115                 120                 125

Gly
```

<210> SEQ ID NO 3
<211> LENGTH: 130
<212> TYPE: PRT
<213> ORGANISM: Artificial Sequence
<220> FEATURE:
<223> OTHER INFORMATION: Artificial Oligonucleotide

<400> SEQUENCE: 3

```
Ile Gln Leu Gln Gln Ser Gly Ala Glu Leu Val Lys Pro Gly Ala Ser
 1               5                  10                  15
```

```
Val Lys Ile Ser Cys Lys Ala Ser Gly Tyr Ser Phe Thr Gly Tyr Asn
             20                  25                  30

Met Asn Trp Val Lys Gln Ser His Gly Lys Ser Leu Glu Trp Ile Gly
         35                  40                  45

Asn Ile Asn Pro Tyr Tyr Gly Ser Thr Ser Tyr Asn Gln Lys Phe Lys
     50                  55                  60

Gly Lys Ala Thr Leu Thr Val Asp Lys Ser Ser Ser Thr Ala Tyr Met
 65                  70                  75                  80

Gln Leu Asn Ser Leu Thr Ser Glu Asp Ser Ala Val Tyr Tyr Cys Ala
                 85                  90                  95

Arg Gly Lys Gly Thr Gly Phe Ala Tyr Trp Gly Gln Gly Thr Leu Val
             100                 105                 110

Thr Val Ser Ala Ala Lys Thr Thr Pro Pro Ser Val Tyr Pro Leu Val
         115                 120                 125

Pro Val
    130

<210> SEQ ID NO 4
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 4

Val Lys Leu Gln Gln Ser Gly Thr Glu Val Val Lys Pro Gly Ala Ser
 1               5                  10                  15

Val Lys Leu Ser
             20

<210> SEQ ID NO 5
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 5

Val Lys Pro Gly Ala Ser Val Lys Leu Ser Cys Lys Ala Ser Gly Tyr
 1               5                  10                  15

Ile Phe Thr Ser
             20

<210> SEQ ID NO 6
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 6

Cys Lys Ala Ser Gly Tyr Ile Phe Thr Ser Tyr Asp Ile Asp Trp Val
 1               5                  10                  15

Arg Gln Thr Pro
             20

<210> SEQ ID NO 7
<211> LENGTH: 20
<212> TYPE: PRT
<213> ORGANISM: Artificial Sequence
<220> FEATURE:
<223> OTHER INFORMATION: Artificial Oligonucleotide
```

```
<400> SEQUENCE: 7

Tyr Asp Ile Asp Trp Val Arg Gln Thr Pro Glu Gln Gly Leu Glu Trp
 1               5                  10                  15

Ile Gly Trp Ile
            20

<210> SEQ ID NO 8
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 8

Glu Gln Gly Leu Glu Trp Ile Gly Trp Ile Phe Pro Gly Glu Gly Ser
 1               5                  10                  15

Thr Glu Tyr Asn
            20

<210> SEQ ID NO 9
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 9

Phe Pro Gly Glu Gly Ser Thr Glu Tyr Asn Glu Lys Phe Lys Gly Arg
 1               5                  10                  15

Ala Thr Leu Ser
            20

<210> SEQ ID NO 10
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 10

Glu Lys Phe Lys Gly Arg Ala Thr Leu Ser Val Asp Lys Ser Ser Ser
 1               5                  10                  15

Thr Ala Tyr Met
            20

<210> SEQ ID NO 11
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 11

Val Asp Lys Ser Ser Ser Thr Ala Tyr Met Glu Leu Thr Arg Leu Thr
 1               5                  10                  15

Ser Glu Asp Ser
            20

<210> SEQ ID NO 12
<211> LENGTH: 20
<212> TYPE: PRT
<213> ORGANISM: Artificial Sequence
<220> FEATURE:
```

-continued

```
<223> OTHER INFORMATION: Artificial Oligonucleotide

<400> SEQUENCE: 12

Glu Leu Thr Arg Leu Thr Ser Glu Asp Ser Ala Val Tyr Phe Cys Ala
 1               5                  10                  15

Arg Gly Asp Tyr
            20

<210> SEQ ID NO 13
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 13

Ala Val Tyr Phe Cys Ala Arg Gly Asp Tyr Asp Tyr Tyr Arg Arg Tyr
 1               5                  10                  15

Phe Asp Leu Trp
            20

<210> SEQ ID NO 14
<211> LENGTH: 19
<212> TYPE: PRT
<213> ORGANISM: Artificial Sequence
<220> FEATURE:
<223> OTHER INFORMATION: Artificial Oligonucleotide

<400> SEQUENCE: 14

Asp Tyr Tyr Arg Arg Tyr Phe Asp Leu Trp Gly Gln Gly Thr Thr Val
 1               5                  10                  15

Thr Val Ser

<210> SEQ ID NO 15
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 15

Asp Ile Val Leu Thr Gln Ser Pro Ala Ser Leu Ala Val Ser Leu Gly
 1               5                  10                  15

Gln Arg Ala Thr
            20

<210> SEQ ID NO 16
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 16

Leu Ala Val Ser Leu Gly Gln Arg Ala Thr Ile Ser Cys Arg Ala Ser
 1               5                  10                  15

Gln Ser Val Ser
            20

<210> SEQ ID NO 17
<211> LENGTH: 20
<212> TYPE: PRT
<213> ORGANISM: Artificial Sequence
<220> FEATURE:
```

<223> OTHER INFORMATION: Artificial Oligonucleotide

<400> SEQUENCE: 17

Ile Ser Cys Arg Ala Ser Gln Ser Val Ser Thr Ser Ser Tyr Ser Tyr
1               5                   10                  15

Met His Trp Tyr
            20

<210> SEQ ID NO 18
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 18

Thr Ser Ser Tyr Ser Tyr Met His Trp Tyr Gln Gln Lys Pro Gly Gln
1               5                   10                  15

Pro Pro Lys Leu
            20

<210> SEQ ID NO 19
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 19

Gln Gln Lys Pro Gly Gln Pro Pro Lys Leu Leu Ile Lys Tyr Ala Ser
1               5                   10                  15

Asn Leu Glu Ser
            20

<210> SEQ ID NO 20
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 20

Leu Ile Lys Tyr Ala Ser Asn Leu Glu Ser Gly Val Pro Ala Arg Phe
1               5                   10                  15

Ser Gly Ser Gly
            20

<210> SEQ ID NO 21
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 21

Gly Val Pro Ala Arg Phe Ser Gly Ser Gly Ser Gly Thr Asp Phe Thr
1               5                   10                  15

Leu Asn Ile His
            20

<210> SEQ ID NO 22
<211> LENGTH: 20
<212> TYPE: PRT
<213> ORGANISM: Artificial Sequence

```
<220> FEATURE:
<223> OTHER INFORMATION: Artificial Oligonucleotide

<400> SEQUENCE: 22

Ser Gly Thr Asp Phe Thr Leu Asn Ile His Pro Val Glu Glu Asp
 1               5                  10                  15

Thr Ala Thr Tyr
            20

<210> SEQ ID NO 23
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 23

Pro Val Glu Glu Glu Asp Thr Ala Thr Tyr Tyr Cys Gln His Ser Trp
 1               5                  10                  15

Glu Ile Pro Tyr
            20

<210> SEQ ID NO 24
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 24

Tyr Cys Gln His Ser Trp Glu Ile Pro Tyr Thr Phe Gly Gly Gly Thr
 1               5                  10                  15

Lys Leu Glu Ile
            20

<210> SEQ ID NO 25
<211> LENGTH: 19
<212> TYPE: PRT
<213> ORGANISM: Artificial Sequence
<220> FEATURE:
<223> OTHER INFORMATION: Artificial Oligonucleotide

<400> SEQUENCE: 25

Thr Phe Gly Gly Gly Thr Lys Leu Glu Ile Lys Arg Ala Asp Ala Ala
 1               5                  10                  15

Pro Ala Val

<210> SEQ ID NO 26
<211> LENGTH: 19
<212> TYPE: PRT
<213> ORGANISM: Artificial Sequence
<220> FEATURE:
<223> OTHER INFORMATION: Artificial Oligonucleotide

<400> SEQUENCE: 26

Lys Arg Ala Asp Ala Ala Pro Ala Val Ser Ile Phe Pro Pro Ser Ser
 1               5                  10                  15

Lys Leu Gly

<210> SEQ ID NO 27
<211> LENGTH: 20
<212> TYPE: PRT
<213> ORGANISM: Artificial Sequence
<220> FEATURE:
```

<223> OTHER INFORMATION: Artificial Oligonucleotide

<400> SEQUENCE: 27

Ile Gln Leu Gln Gln Ser Gly Ala Glu Leu Val Lys Pro Gly Ala Ser
1               5                   10                  15

Val Lys Ile Ser
            20

<210> SEQ ID NO 28
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 28

Val Lys Pro Gly Ala Ser Val Lys Ile Ser Cys Lys Ala Ser Gly Tyr
1               5                   10                  15

Ser Phe Thr Gly
            20

<210> SEQ ID NO 29
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 29

Cys Lys Ala Ser Gly Tyr Ser Phe Thr Gly Tyr Asn Met Asn Trp Val
1               5                   10                  15

Lys Gln Ser His
            20

<210> SEQ ID NO 30
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 30

Tyr Asn Met Asn Trp Val Lys Gln Ser His Gly Lys Ser Leu Glu Trp
1               5                   10                  15

Ile Gly Asn Ile
            20

<210> SEQ ID NO 31
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 31

Gly Lys Ser Leu Glu Trp Ile Gly Asn Ile Asn Pro Tyr Tyr Gly Ser
1               5                   10                  15

Thr Ser Tyr Asn
            20

<210> SEQ ID NO 32
<211> LENGTH: 20
<212> TYPE: PRT
<213> ORGANISM: Artificial Sequence

```
<220> FEATURE:
<223> OTHER INFORMATION: Artificial Oligonucleotide

<400> SEQUENCE: 32

Asn Pro Tyr Tyr Gly Ser Thr Ser Tyr Asn Gln Lys Phe Lys Gly Lys
 1               5                  10                  15

Ala Thr Leu Thr
            20

<210> SEQ ID NO 33
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 33

Gln Lys Phe Lys Gly Lys Ala Thr Leu Thr Val Asp Lys Ser Ser Ser
 1               5                  10                  15

Thr Ala Tyr Met
            20

<210> SEQ ID NO 34
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 34

Val Asp Lys Ser Ser Ser Thr Ala Tyr Met Gln Leu Asn Ser Leu Thr
 1               5                  10                  15

Ser Glu Asp Ser
            20

<210> SEQ ID NO 35
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 35

Gln Leu Asn Ser Leu Thr Ser Glu Asp Ser Ala Val Tyr Tyr Cys Ala
 1               5                  10                  15

Arg Gly Lys Gly
            20

<210> SEQ ID NO 36
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 36

Ala Val Tyr Tyr Cys Ala Arg Gly Lys Gly Thr Gly Phe Ala Tyr Trp
 1               5                  10                  15

Gly Gln Gly Thr
            20

<210> SEQ ID NO 37
<211> LENGTH: 20
<212> TYPE: PRT
```

```
<213> ORGANISM: Artificial Sequence
<220> FEATURE:
<223> OTHER INFORMATION: Artificial Oligonucleotide

<400> SEQUENCE: 37

Thr Gly Phe Ala Tyr Trp Gly Gln Gly Thr Leu Val Thr Val Ser Ala
 1               5                  10                  15

Ala Lys Thr Thr
            20

<210> SEQ ID NO 38
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 38

Leu Val Thr Val Ser Ala Ala Lys Thr Thr Pro Pro Ser Val Tyr Pro
 1               5                  10                  15

Leu Val Pro Val
            20

<210> SEQ ID NO 39
<211> LENGTH: 19
<212> TYPE: PRT
<213> ORGANISM: Artificial Sequence
<220> FEATURE:
<223> OTHER INFORMATION: Artificial Oligonucleotide

<400> SEQUENCE: 39

Lys Pro Gly Ala Ser Val Lys Leu Ser Cys Lys Ala Ser Gly Tyr Ile
 1               5                  10                  15

Phe Thr Ser

<210> SEQ ID NO 40
<211> LENGTH: 18
<212> TYPE: PRT
<213> ORGANISM: Artificial Sequence
<220> FEATURE:
<223> OTHER INFORMATION: Artificial Oligonucleotide

<400> SEQUENCE: 40

Pro Gly Ala Ser Val Lys Leu Ser Cys Lys Ala Ser Gly Tyr Ile Phe
 1               5                  10                  15

Thr Ser

<210> SEQ ID NO 41
<211> LENGTH: 17
<212> TYPE: PRT
<213> ORGANISM: Artificial Sequence
<220> FEATURE:
<223> OTHER INFORMATION: Artificial Oligonucleotide

<400> SEQUENCE: 41

Gly Ala Ser Val Lys Leu Ser Cys Lys Ala Ser Gly Tyr Ile Phe Thr
 1               5                  10                  15

Ser

<210> SEQ ID NO 42
<211> LENGTH: 16
<212> TYPE: PRT
<213> ORGANISM: Artificial Sequence
<220> FEATURE:
```

<223> OTHER INFORMATION: Artificial Oligonucleotide

<400> SEQUENCE: 42

Ala Ser Val Lys Leu Ser Cys Lys Ala Ser Gly Tyr Ile Phe Thr Ser
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: Artificial Oligonucleotide

<400> SEQUENCE: 43

Ser Val Lys Leu Ser Cys Lys Ala Ser Gly Tyr Ile Phe Thr Ser
 1               5                  10                  15

<210> SEQ ID NO 44
<211> LENGTH: 14
<212> TYPE: PRT
<213> ORGANISM: Artificial Sequence
<220> FEATURE:
<223> OTHER INFORMATION: Artificial Oligonucleotide

<400> SEQUENCE: 44

Val Lys Leu Ser Cys Lys Ala Ser Gly Tyr Ile Phe Thr Ser
 1               5                  10

<210> SEQ ID NO 45
<211> LENGTH: 13
<212> TYPE: PRT
<213> ORGANISM: Artificial Sequence
<220> FEATURE:
<223> OTHER INFORMATION: Artificial Oligonucleotide

<400> SEQUENCE: 45

Lys Leu Ser Cys Lys Ala Ser Gly Tyr Ile Phe Thr Ser
 1               5                  10

<210> SEQ ID NO 46
<211> LENGTH: 12
<212> TYPE: PRT
<213> ORGANISM: Artificial Sequence
<220> FEATURE:
<223> OTHER INFORMATION: Artificial Oligonucleotide

<400> SEQUENCE: 46

Leu Ser Cys Lys Ala Ser Gly Tyr Ile Phe Thr Ser
 1               5                  10

<210> SEQ ID NO 47
<211> LENGTH: 11
<212> TYPE: PRT
<213> ORGANISM: Artificial Sequence
<220> FEATURE:
<223> OTHER INFORMATION: Artificial Oligonucleotide

<400> SEQUENCE: 47

Ser Cys Lys Ala Ser Gly Tyr Ile Phe Thr Ser
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: Artificial Oligonucleotide

<400> SEQUENCE: 48

Cys Lys Ala Ser Gly Tyr Ile Phe Thr Ser
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Artificial Oligonucleotide

<400> SEQUENCE: 49

Lys Ala Ser Gly Tyr Ile Phe Thr Ser
1               5

<210> SEQ ID NO 50
<211> LENGTH: 8
<212> TYPE: PRT
<213> ORGANISM: Artificial Sequence
<220> FEATURE:
<223> OTHER INFORMATION: Artificial Oligonucleotide

<400> SEQUENCE: 50

Ala Ser Gly Tyr Ile Phe Thr Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Artificial Oligonucleotide

<400> SEQUENCE: 51

Ser Gly Tyr Ile Phe Thr Ser
1               5

<210> SEQ ID NO 52
<211> LENGTH: 6
<212> TYPE: PRT
<213> ORGANISM: Artificial Sequence
<220> FEATURE:
<223> OTHER INFORMATION: Artificial Oligonucleotide

<400> SEQUENCE: 52

Gly Tyr Ile Phe Thr Ser
1               5

<210> SEQ ID NO 53
<211> LENGTH: 19
<212> TYPE: PRT
<213> ORGANISM: Artificial Sequence
<220> FEATURE:
<223> OTHER INFORMATION: Artificial Oligonucleotide

<400> SEQUENCE: 53

Ser Cys Arg Ala Ser Gln Ser Val Ser Thr Ser Ser Tyr Ser Tyr Met
1               5                   10                  15

His Trp Tyr

<210> SEQ ID NO 54
<211> LENGTH: 18
<212> TYPE: PRT
<213> ORGANISM: Artificial Sequence
<220> FEATURE:

```
<223> OTHER INFORMATION: Artificial Oligonucleotide

<400> SEQUENCE: 54

Cys Arg Ala Ser Gln Ser Val Ser Thr Ser Ser Tyr Ser Tyr Met His
 1               5                  10                  15

Trp Tyr

<210> SEQ ID NO 55
<211> LENGTH: 17
<212> TYPE: PRT
<213> ORGANISM: Artificial Sequence
<220> FEATURE:
<223> OTHER INFORMATION: Artificial Oligonucleotide

<400> SEQUENCE: 55

Arg Ala Ser Gln Ser Val Ser Thr Ser Ser Tyr Ser Tyr Met His Trp
 1               5                  10                  15

Tyr

<210> SEQ ID NO 56
<211> LENGTH: 16
<212> TYPE: PRT
<213> ORGANISM: Artificial Sequence
<220> FEATURE:
<223> OTHER INFORMATION: Artificial Oligonucleotide

<400> SEQUENCE: 56

Ala Ser Gln Ser Val Ser Thr Ser Ser Tyr Ser Tyr Met His Trp Tyr
 1               5                  10                  15

<210> SEQ ID NO 57
<211> LENGTH: 15
<212> TYPE: PRT
<213> ORGANISM: Artificial Sequence
<220> FEATURE:
<223> OTHER INFORMATION: Artificial Oligonucleotide

<400> SEQUENCE: 57

Ser Gln Ser Val Ser Thr Ser Ser Tyr Ser Tyr Met His Trp Tyr
 1               5                  10                  15

<210> SEQ ID NO 58
<211> LENGTH: 14
<212> TYPE: PRT
<213> ORGANISM: Artificial Sequence
<220> FEATURE:
<223> OTHER INFORMATION: Artificial Oligonucleotide

<400> SEQUENCE: 58

Gln Ser Val Ser Thr Ser Ser Tyr Ser Tyr Met His Trp Tyr
 1               5                  10

<210> SEQ ID NO 59
<211> LENGTH: 13
<212> TYPE: PRT
<213> ORGANISM: Artificial Sequence
<220> FEATURE:
<223> OTHER INFORMATION: Artificial Oligonucleotide

<400> SEQUENCE: 59

Ser Val Ser Thr Ser Ser Tyr Ser Tyr Met His Trp Tyr
 1               5                  10

<210> SEQ ID NO 60
<211> LENGTH: 12
```

```
<212> TYPE: PRT
<213> ORGANISM: Artificial Sequence
<220> FEATURE:
<223> OTHER INFORMATION: Artificial Oligonucleotide

<400> SEQUENCE: 60

Val Ser Thr Ser Ser Tyr Ser Tyr Met His Trp Tyr
 1               5                  10

<210> SEQ ID NO 61
<211> LENGTH: 11
<212> TYPE: PRT
<213> ORGANISM: Artificial Sequence
<220> FEATURE:
<223> OTHER INFORMATION: Artificial Oligonucleotide

<400> SEQUENCE: 61

Ser Thr Ser Ser Tyr Ser Tyr Met His Trp Tyr
 1               5                  10

<210> SEQ ID NO 62
<211> LENGTH: 10
<212> TYPE: PRT
<213> ORGANISM: Artificial Sequence
<220> FEATURE:
<223> OTHER INFORMATION: Artificial Oligonucleotide

<400> SEQUENCE: 62

Thr Ser Ser Tyr Ser Tyr Met His Trp Tyr
 1               5                  10

<210> SEQ ID NO 63
<211> LENGTH: 9
<212> TYPE: PRT
<213> ORGANISM: Artificial Sequence
<220> FEATURE:
<223> OTHER INFORMATION: Artificial Oligonucleotide

<400> SEQUENCE: 63

Ser Ser Tyr Ser Tyr Met His Trp Tyr
 1               5

<210> SEQ ID NO 64
<211> LENGTH: 7
<212> TYPE: PRT
<213> ORGANISM: Artificial Sequence
<220> FEATURE:
<223> OTHER INFORMATION: Artificial Oligonucleotide

<400> SEQUENCE: 64

Tyr Ser Tyr Met His Trp Tyr
 1               5

<210> SEQ ID NO 65
<211> LENGTH: 6
<212> TYPE: PRT
<213> ORGANISM: Artificial Sequence
<220> FEATURE:
<223> OTHER INFORMATION: Artificial Oligonucleotide

<400> SEQUENCE: 65

Ser Tyr Met His Trp Tyr
 1               5

<210> SEQ ID NO 66
<211> LENGTH: 16
<212> TYPE: PRT
```

```
<213> ORGANISM: Artificial Sequence
<220> FEATURE:
<223> OTHER INFORMATION: Artificial Oligonucleotide

<400> SEQUENCE: 66

Pro Gly Ala Ser Val Arg Ile Ser Cys Lys Ala Ser Gly Tyr Ala Phe
 1               5                  10                  15

<210> SEQ ID NO 67
<211> LENGTH: 18
<212> TYPE: PRT
<213> ORGANISM: Artificial Sequence
<220> FEATURE:
<223> OTHER INFORMATION: Artificial Oligonucleotide

<400> SEQUENCE: 67

Lys Pro Gly Asp Ser Leu Arg Leu Ser Cys Lys Ala Ser Gly Tyr Thr
 1               5                  10                  15

Phe Ser

<210> SEQ ID NO 68
<211> LENGTH: 20
<212> TYPE: PRT
<213> ORGANISM: Artificial Sequence
<220> FEATURE:
<223> OTHER INFORMATION: Artificial Oligonucleotide

<400> SEQUENCE: 68

Val Lys Pro Gly Gly Ser Leu Arg Leu Ser Cys Val Ala Ser Gly Phe
 1               5                  10                  15

Thr Phe Ser Ser
            20

<210> SEQ ID NO 69
<211> LENGTH: 19
<212> TYPE: PRT
<213> ORGANISM: Artificial Sequence
<220> FEATURE:
<223> OTHER INFORMATION: Artificial Oligonucleotide

<400> SEQUENCE: 69

Lys Pro Gly Asp Ser Leu Arg Leu Ser Cys Lys Gly Ser Gly Phe Thr
 1               5                  10                  15

Phe Ser Asn

<210> SEQ ID NO 70
<211> LENGTH: 21
<212> TYPE: PRT
<213> ORGANISM: Artificial Sequence
<220> FEATURE:
<223> OTHER INFORMATION: Artificial Oligonucleotide

<400> SEQUENCE: 70

Lys Leu Ser Cys Lys Ala Ser Gly Tyr Ile Phe Thr Ser Glu His Arg
 1               5                  10                  15

Gly Gly Pro Glu Glu
            20

<210> SEQ ID NO 71
<211> LENGTH: 21
<212> TYPE: PRT
<213> ORGANISM: Artificial Sequence
<220> FEATURE:
<223> OTHER INFORMATION: Artificial Oligonucleotide
```

-continued

```
<400> SEQUENCE: 71

Lys Leu Ser Cys Lys Ala Ser Gly Tyr Ile Phe Thr Ser His Arg Gly
  1               5                  10                  15

Gly Pro Glu Glu Phe
            20

<210> SEQ ID NO 72
<211> LENGTH: 21
<212> TYPE: PRT
<213> ORGANISM: Artificial Sequence
<220> FEATURE:
<223> OTHER INFORMATION: Artificial Oligonucleotide

<400> SEQUENCE: 72

Lys Leu Ser Cys Lys Ala Ser Gly Tyr Ile Phe Thr Ser Arg Gly Gly
  1               5                  10                  15

Pro Glu Glu Phe Glu
            20

<210> SEQ ID NO 73
<211> LENGTH: 21
<212> TYPE: PRT
<213> ORGANISM: Artificial Sequence
<220> FEATURE:
<223> OTHER INFORMATION: Artificial Oligonucleotide

<400> SEQUENCE: 73

Val Lys Leu Ser Cys Lys Ala Ser Gly Tyr Ile Phe Thr Ser Glu His
  1               5                  10                  15

Arg Gly Gly Pro Glu
            20

<210> SEQ ID NO 74
<211> LENGTH: 21
<212> TYPE: PRT
<213> ORGANISM: Artificial Sequence
<220> FEATURE:
<223> OTHER INFORMATION: Artificial Oligonucleotide

<400> SEQUENCE: 74

Val Lys Leu Ser Cys Lys Ala Ser Gly Tyr Ile Phe Thr Ser His Arg
  1               5                  10                  15

Gly Gly Pro Glu Glu
            20

<210> SEQ ID NO 75
<211> LENGTH: 21
<212> TYPE: PRT
<213> ORGANISM: Artificial Sequence
<220> FEATURE:
<223> OTHER INFORMATION: Artificial Oligonucleotide

<400> SEQUENCE: 75

Val Lys Leu Ser Cys Lys Ala Ser Gly Tyr Ile Phe Thr Ser His Arg
  1               5                  10                  15

Gly Gly Pro Glu Glu
            20

<210> SEQ ID NO 76
<211> LENGTH: 21
<212> TYPE: PRT
<213> ORGANISM: Artificial Sequence
<220> FEATURE:
<223> OTHER INFORMATION: Artificial Oligonucleotide
```

-continued

```
<400> SEQUENCE: 76

Val Lys Leu Ser Cys Lys Ala Ser Gly Tyr Ile Phe Thr Ser Gly Gly
1               5                   10                  15

Pro Glu Glu Phe Glu
            20

<210> SEQ ID NO 77
<211> LENGTH: 4
<212> TYPE: PRT
<213> ORGANISM: Artificial Sequence
<220> FEATURE:
<223> OTHER INFORMATION: Artificial Oligonucleotide

<400> SEQUENCE: 77

Cys Lys Ala Ser
1

<210> SEQ ID NO 78
<211> LENGTH: 4
<212> TYPE: PRT
<213> ORGANISM: Artificial Sequence
<220> FEATURE:
<223> OTHER INFORMATION: Artificial Oligonucleotide

<400> SEQUENCE: 78

Cys Arg Ala Ser
1
```